(12) United States Patent
Cheng et al.

(10) Patent No.: US 6,833,380 B2
(45) Date of Patent: Dec. 21, 2004

(54) COMPOUNDS THAT MODULATE PPAR ACTIVITY AND METHODS OF PREPARATION

(75) Inventors: Xue-Min Cheng, Ann Arbor, MI (US); Noe Erasga, Ann Arbor, MI (US); Gary Frederick Filzen, Ann Arbor, MI (US); Andrew Geyer, Novi, MI (US); Chitase Lee, Ann Arbor, MI (US); Bharat Kalidas Trivedi, Farmington Hills, MI (US)

(73) Assignee: Warner-Lambert Company, LLC, Morris Plains, NJ (US)

(*) Notice: Subject to any disclaimer, the term of this patent is extended or adjusted under 35 U.S.C. 154(b) by 0 days.

(21) Appl. No.: 10/324,278

(22) Filed: Dec. 19, 2002

(65) Prior Publication Data

US 2003/0207916 A1 Nov. 6, 2003

Related U.S. Application Data

(60) Provisional application No. 60/362,400, filed on Mar. 7, 2002.

(51) Int. Cl.[7] ...................... A61K 31/42; A61K 31/425; C07D 277/02
(52) U.S. Cl. ...................... 514/365; 514/374; 548/203; 548/204; 548/235
(58) Field of Search ................. 548/203, 204, 548/235; 514/365, 374

(56) References Cited

U.S. PATENT DOCUMENTS

| 2003/0207915 A1 | 11/2003 | Cheng et al. |
| 2003/0207924 A1 | 11/2003 | Cheng et al. |
| 2003/0225158 A1 | 12/2003 | Auerbach et al. |

FOREIGN PATENT DOCUMENTS

| EP | 0930299 A1 | 7/1999 |
| WO | WO 97/28137 A1 | 8/1997 |
| WO | WO 97/28149 A1 | 8/1997 |
| WO | WO 01/00603 A1 | 1/2001 |
| WO | WO 01/16120 A1 | 3/2001 |
| WO | WO/01016120 A1 | 3/2001 |
| WO | WO 02/16331 A1 | 2/2002 |
| WO | WO/02016331 A1 | 2/2002 |
| WO | WO/02/18355 A1 | 3/2002 |
| WO | WO 02/50047 A1 | 6/2002 |
| WO | WO 02/50048 A1 | 6/2002 |
| WO | WO 02/062774 A1 | 8/2002 |
| WO | WO 02/092590 A1 | 11/2002 |
| WO | WO/02/096904 A1 | 12/2002 |
| WO | WO 02/100403 A1 | 12/2002 |
| WO | WO02/102780 A1 | 12/2002 |
| WO | WO03/011842 A1 | 2/2003 |
| WO | WO 03/024395 A2 | 3/2003 |

OTHER PUBLICATIONS

T. Gordon et al., The American Journal of Medicine, 1977;62:707–714.
G. Romussi et al., J. Heterocyclic Chem., 13, 211 (1976).
W.R. Oliver et al., PNAS, vol. 98, pp. 5306–5311, (2001).
S.M. Berge et al., "Pharmaceutical Salts", Journal of Pharmaceutical Sciences, 1977;66:1–19.

*Primary Examiner*—Zinna Northington Davis
(74) *Attorney, Agent, or Firm*—Michelle A. Sherwood

(57) ABSTRACT

This invention discloses compounds that alter PPAR activity. The invention also discloses pharmaceutically acceptable salts of the compounds, pharmaceutically acceptable compositions comprising the compounds or their salts, and methods of using them as therapeutic agents for treating or preventing hyperlipidemia and hypercholesteremia in a mammal. The present invention also discloses method for making the disclosed compounds.

30 Claims, No Drawings

COMPOUNDS THAT MODULATE PPAR ACTIVITY AND METHODS OF PREPARATION

CROSS REFERENCE TO RELATED APPLICATION

This Utility Application claims benefit of U.S. Provisional Application Ser. No. 60/362,400 filed Mar. 7, 2002.

FIELD OF THE INVENTION

The present invention relates to compounds and pharmaceutical formulations that can be used to treat conditions mediated by nuclear hormone receptors, more specifically, to compounds and pharmaceutical formulations that modulate PPAR activity.

BACKGROUND OF THE INVENTION

Hypercholesterolemia, hyperlipidemia, and diabetes are well recognized risk factors in the onset of atherosclerosis and coronary heart disease. Hypercholesterolemia and hyperlipidemia are characterized by excessively high levels of blood cholesterol and lipids. The blood cholesterol pool is generally dependent on dietary uptake of cholesterol from the intestine and biosynthesis of cholesterol throughout the body, especially the liver. The majority of cholesterol in plasma is carried on apolipoprotein B-containing lipoproteins, such as low-density lipoproteins (LDL) and very-low-density lipoproteins (VLDL). The risk of coronary artery disease in man increases when LDL and VLDL levels increase. Conversely, high levels of cholesterol carried in high-density lipoproteins (HDL) is protective against coronary artery disease (Am. J. Med., 1977; 62:707–714).

The statins represent perhaps the most important class of lipid-lowering drugs. These compounds inhibit HMG-CoA reductase which is implicated in the rate-limiting step in cellular cholesterol biosynthesis. Representative statins include atorvastatin, lovastatin, pravastatin, and simvastatin. The effectiveness of these compounds depends on LDL receptor regulation. Other important antilipidemia drugs include fibrates such as gemfibril and clofibrate, bile acid sequestrants such as cholestyramine and colestipol, probucol, and nicotinic acid analogs.

To date, a number of oral antidiabetic agents have been developed. The most commonly used hypoglygemic drugs are the sulfonylureas. Sulfonylureas are generally used to stimulate insulin. The biguanide metformin is generally used to improve insulin sensitivity and to decrease hepatic glucose output. Acarbose is used to limit postprandial hyperglycemia. Thiazolidine 2,4 diones are used to enhance insulin action without increasing insulin secretion.

Peroxisome Proliferator Activation Receptors (PPAR) are implicated in a number of biological processes and disease states including hypercholesterolemia, hyperlipidemia, and diabetes. PPARs are members of the nuclear receptor superfamily of transcription factors that includes steroid, thyroid, and vitamin D receptors. They play a role in controlling expression of proteins that regulate lipid metabolism. Furthermore, the PPARs are activated by fatty acids and fatty acid metabolites. There are three PPAR subtypes PPAR α, PPAR β (also referred to as PPAR δ), and PPAR γ. Each receptor shows a different pattern of tissue expression, and differences in activation by structurally diverse compounds. PPAR γ, for instance, is expressed most abundantly in adipose tissue and at lower levels in skeletal muscle, heart, liver, intestine, kidney, vascular endothelial and smooth muscle cells as well as macrophages. PPAR receptors are associated with regulation of insulin sensitivity and blood glucose levels, macrophage differentiation, inflammatory response, and cell differentiation. Accordingly, PPARs have been associated with obesity, diabetes, carcinogenesis, hyperplasia, atherosclerosis, hyperlipidemia, and hypercholesterolemia.

In addition, PPARα agonists lower plasma triglycerides and LDL cholesterol and are therefore useful in treating hypertriglyceridemia, hyperlipidemia and obesity. PPAR γ is associated with the development of non-insulin-dependent diabetes mellitus (NIDDM), hypertension, coronary artery disease, hyperlipidemia and certain malignancies. Finally, activation of PPAR β has been demonstrated to increase HDL levels. (Leibowitz, WO97/28149, August 1997.) More recently, a PPAR β selective agonist was reported to have shown a dose-related increase in serum HDL-C and decrease in LDL-C and VLDL-TG in insulin-resistant middle aged rhesus monkeys. (W. R. Oliver et al., PNAS, v. 98, pp. 5306–5311, 2001)

Antilipidemic and antidiabetic agents are still considered to have non-uniform effectiveness. The effectiveness of antidiabetic and antilipidemic therapies is limited, in part because of poor patient compliance due to unacceptable side effects. These side effects include diarrhea and gastrointestinal discomfort, and in the case of antidiabetics, edema, hypoglycemia and hepatoxicity. Furthermore, each type of drug does not work equally well in all patients.

For the reasons set forth above, there is a need for novel antilipidemic and antidiabetic agents that can be used alone or in combination. Furthermore, activation of PPARβ alone or in combination with the simultaneous activation of PPAR α and/or PPAR γ may be desirable in formulating a treatment for dyslipidemia.

SUMMARY OF THE INVENTION

The present invention provides compounds capable of altering PPAR activity. Compounds of the present invention are described by Formula I:

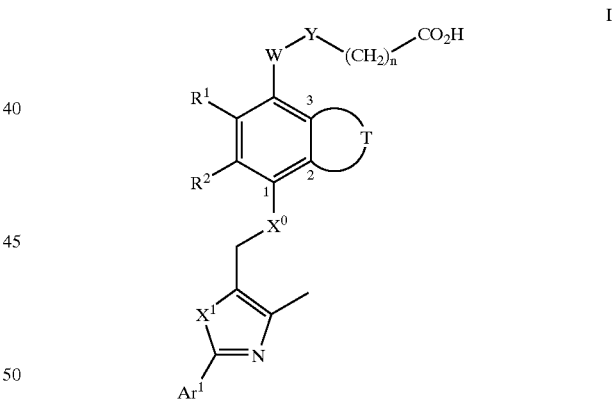

or a pharmaceutically acceptable salt thereof, where:

T is a saturated or unsaturated, substituted or unsubstituted hydrocarbon chain or hydrocarbon-heteroatom chain having from 3 to 6 atoms wherein the carbon atom of position 2 is connected to the carbon atom of position 3 to form a five to eight member ring;

W is O, S, $CH_2$, $CR^4R^5$, $NR^3$, cycloalkylene, or heterocycloalkylene;

Y is absent, O, or $CR^4R^5$ where

Y is $CR^4R^5$ or absent when W is O, S, or $NR^3$; and

Y is O or absent when W is $CH_2$ or $CR^4R^5$;

$R^1$ and $R^2$ are independently hydrogen, lower alkyl, lower alkoxy, haloalkyl, —O—$(CH_2)_pCF_3$, halogen, nitro, cyano, —OH, —SH, —$CF_3$, —$S(O)_p$alkyl, $S(O)_p$aryl, —$(CH_2)_m$ $OR^3$, —$(CH_2)_mNR^6R^7$, —$COR^3$, —$CO_2H$, —$CO_2R^3$, or —$NR^6R^7$;

$R^3$ is hydrogen, alkyl, alkenyl, alkynyl, or aryl;

$R^4$ and $R^5$ are independently hydrogen, alkyl, alkenyl, alkynyl, or aryl, or joined together to form a 4 to 7 member ring having 0 to 3 heteroatoms;

$R^6$ and $R^7$ are independently hydrogen, alkyl, alkenyl, alkynyl, —COalkyl, —COaryl, cycloalkyl, —$CO_2$alkyl, —$CO_2$aryl, —$SO_2$alkyl, —$SO_2$aryl, or joined together to form a 4 to 7 member ring having 1 to 3 heteroatoms;

$X^0$ and $X^1$ are independently O or S;

$Ar^1$ is substituted or unsubstituted aryl or heteroaryl;

m is 0 to 5;

n is 0 to 5; and p is 0 to 2.

In one embodiment, the present invention provides compounds as described by Formula IIa, Formula IIb, Formula IIc, Formula IId, or Formula IIe:

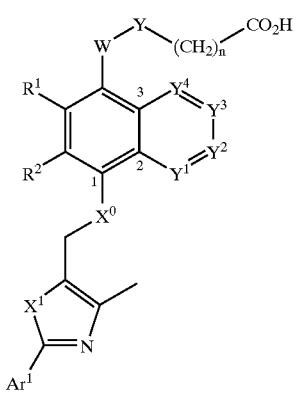

IIa

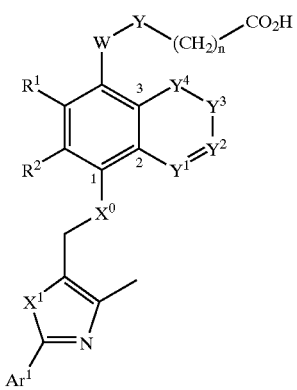

IIb

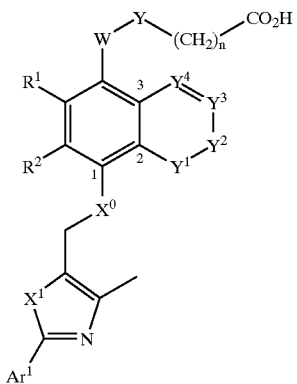

IIc

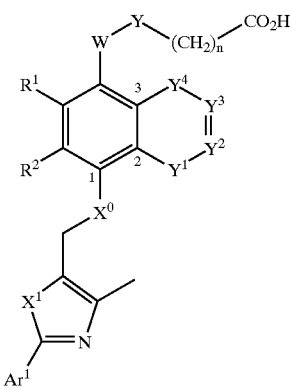

IId

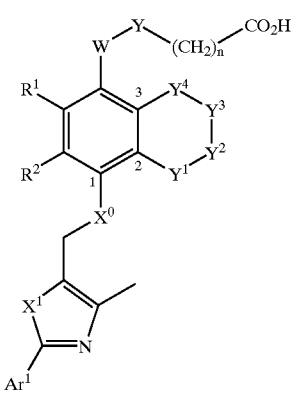

IIe or a pharmaceutically acceptable salt thereof, where:

W is O, S, $CH_2$, $CR^4R^5$, $NR^3$, cycloalkylene, or heterocycloalkylene;

Y is absent, O, or $CR^4R^5$ where

Y is $CR^4R^5$ or absent when W is O, S, or $NR^3$; and

Y is O or absent when W is $CH_2$ or $CR^4R^5$;

$R^1$ and $R^2$ are independently hydrogen, lower alkyl, lower alkoxy, haloalkyl, —O—$(CH_2)_pCF_3$, halogen, nitro, cyano, —OH, —SH, —$CF_3$, —$S(O)_p$alkyl, $S(O)_p$aryl, —$(CH_2)_m$$OR^3$, —$(CH_2)_mNR^6R^7$, —$COR^3$, —$CO_2H$, —$CO_2R^3$, or —$NR^6R^7$;

$R^3$ is hydrogen, alkyl, alkenyl, alkynyl, or aryl;

$R^4$ and $R^5$ are independently hydrogen, alkyl, alkenyl, alkynyl, or aryl, or joined together to form a 4 to 7 member ring having 0 to 3 heteroatoms;

$R^6$ and $R^7$ are independently hydrogen, alkyl, alkenyl, alkynyl, —COalkyl, —COaryl, cycloalkyl, —$CO_2$alkyl, —$CO_2$aryl, —$SO_2$alkyl, —$SO_2$aryl, or joined together to form a 4 to 7 member ring having 1 to 3 heteroatoms;

$X^0$ and $X^1$ are independently O or S;

$Ar^1$ is substituted or unsubstituted aryl or heteroaryl;

m is 0 to 5;

n is 0 to 5;

p is 0 to 2; and $Y^1$, $Y^2$, $Y^3$ and $Y^4$ are independently a carbon atom or a heteroatom wherein the carbon atom and the heteroatom are bonded to a sufficient number of hydrogen atoms or substituents to complete the valency of each atom with the proviso that $Y^1$, $Y^2$, $Y^3$ and $Y^4$ are not all heteroatoms and that not more than two adjacent atoms in $Y^1$, $Y^2$, $Y^3$ and $Y^4$ are heteroatoms and that in Formulae IIb, IIc, and IId, $Y^1$, $Y^2$, $Y^3$ and $Y^4$ are not all carbon.

In one embodiment, the present invention provides compounds as described by Formula IIIa or Formula IIIb:

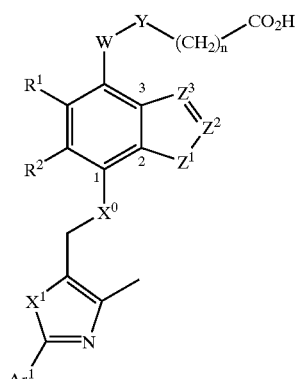

IIIa

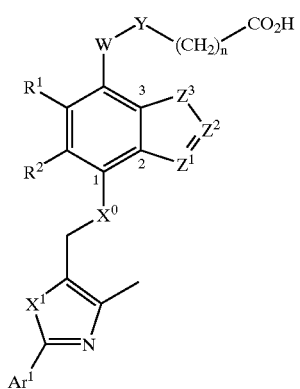

IIIb

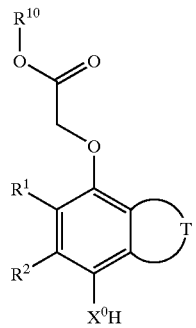

IIIc or a pharmaceutically acceptable salt thereof, where:

W is O, S, $CH_2$, $CR^4R^5$, $NR^3$, cycloalkylene, or heterocycloalkylene;

Y is absent, O, or $CR^4R^5$ where

Y is $CR^4R^5$ or absent when W is O, S, or $NR^3$; and

Y is O or absent when W is $CH_2$ or $CR^4R^5$;

$R^1$ and $R^2$ are independently hydrogen, lower alkyl, lower alkoxy, haloalkyl, —O—$(CH_2)_p CF_3$, halogen, nitro, cyano, —OH, —SH, —$CF_3$, —$S(O)_p$alkyl, $S(O)_p$aryl, —$(CH_2)_m OR^3$, —$(CH_2)_m NR^6R^7$, —$COR^3$, —$CO_2H$, —$CO_2R^3$, or —$NR^6R^7$;

$R^3$ is hydrogen, alkyl, alkenyl, alkynyl, or aryl;

$R^4$ and $R^5$ are independently hydrogen, alkyl, alkenyl, alkynyl, or aryl, or joined together to form a 4 to 7 member ring having 0 to 3 heteroatoms;

$R^6$ and $R^7$ are independently hydrogen, alkyl, alkenyl, alkynyl, —COalkyl, —COaryl, cycloalkyl, —$CO_2$alkyl, —$CO_2$aryl, —$SO_2$alkyl, —$SO_2$aryl, or joined together to form a 4 to 7 member ring having 1 to 3 heteroatoms;

$X^0$ and $X^1$ are independently O or S;

$Ar^1$ is substituted or unsubstituted aryl or heteroaryl;

m is 0 to 5;

n is 0 to 5;

p is 0 to 2; and $Z^1$, $Z^2$, and $Z^3$ are independently a carbon atom or a heteroatom wherein the carbon atom and the heteroatom are bonded to a sufficient number of hydrogen atoms or substituents to complete the valency of each atom with the proviso that $Z^1$, $Z^2$, and $Z^3$ are not all heteroatoms and that in Formulae IIIa and IIIb $Z^1$, $Z^2$, and $Z^3$ are not all carbon atoms.

In yet another embodiment of the present invention, a method of preparing the compounds of Formula I–III is provided. The method of the present invention includes reacting

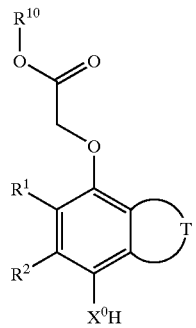

in a solvent in the presence of a base such as cesium carbonate, with

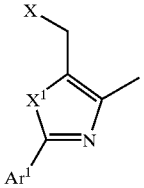

where

T, $R^1$, $R^2$, $R^3$, $R^4$, $R^5$, $R^6$, $R^7$, $X^0$, $X^1$, $Ar^1$, m, n, and p are the same as described above;

X is a halogen; and $R^{10}$ is a lower alkyl.

In another embodiment of the present invention a pharmaceutical composition comprising a compound of Formula I and one or more pharmaceutically acceptable carriers, diluents, or excipients is provided.

In another embodiment of the present invention, a method of treating, preventing or controlling hypercholesteremia in a mammal is provided. The method comprises administering to the mammal in need thereof a therapeutically effective amount of the compounds of the present invention.

In another embodiment of the present invention a method for treating, preventing, or controlling obesity is provided.

In another embodiment of the present invention a method for treating, preventing, or controlling hyperglycemia is provided.

In another embodiment of the present invention a method for treating, preventing, or controlling atherosclerosis is provided.

In another embodiment of the present invention a method for treating, preventing, or controlling hypertriglyceridemia is provided.

In another embodiment of the present invention a method for treating, preventing, or controlling hyperinsulinemia is provided.

In another embodiment of the present invention a method for treating, preventing, or controlling diabetes is provided.

In another embodiment of the present invention a method for treating a patient exhibiting glucose disorders associated with circulating glucocorticoids, growth hormone, catecholamines, glucagon, or parathyroid hormone is provided.

For each disease state treatable, preventable, or controllable by the method of the present invention, a therapeutically effective amount of the compounds of the present invention are administered to the mammal in need thereof.

In yet another embodiment of the present invention, a method for preparing compounds of Formula I is provided.

DETAILED DESCRIPTION OF THE INVENTION

The following definitions are used, unless otherwise described: alkyl, alkoxy, alkenyl, alkynyl, etc. denote both straight and branched groups; but reference to an individual radical such as "propyl" embraces only the straight chain radical, a branched chain isomer such as "isopropyl" being specifically referred to.

The term "alkyl" as used herein refers to a straight or branched hydrocarbon of from 1 to 11 carbon atoms and includes, for example, methyl, ethyl, n-propyl, isopropyl, n-butyl, sec-butyl, isobutyl, tert-butyl, n-pentyl, n-hexyl, and the like. The alkyl group can also be substituted with one or more of the substituents selected from lower alkoxy, lower thioalkoxy, —O(CH$_2$)$_{0-2}$CF$_3$, halogen, nitro, cyano, =O, =S, —OH, —SH, —CF$_3$, —CO$_2$H, —CO$_2$C$_1$–C$_6$ alkyl, —NH$_2$, —NHC$_1$–C$_6$ alkyl, —CONR'R", or —N(C$_1$–C$_6$alkyl)$_2$ where R' and R" are independently alkyl, akenyl, alkynyl, aryl, or joined together to form a 4 to 7 member ring. Useful alkyl groups have from 1 to 6 carbon atoms (C$_1$–C$_6$ alkyl).

The term "lower alkyl" as used herein refers to a subset of alkyl which means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like. Optionally, lower alkyl is referred to as "C$_1$–C$_6$alkyl."

The term "alkenyl" means a straight or branched unsaturated hydrocarbon radical having from 2 to 12 carbon atoms and includes, for example, ethenyl, 1-propenyl, 2-propenyl, 1-butenyl, 2-butenyl, 1-pentenyl, 2-pentenyl, 3-methyl-3-butenyl, 1-hexenyl, 2-hexenyl, 3-hexenyl, 3-heptenyl, 1-octenyl, 1-nonenyl, 1-decenyl, 1-undecenyl, 1-dodecenyl, and the like.

The term "alkynyl" means a straight or branched hydrocarbon radical having from 2 to 12 carbon atoms having at least one triple bond and includes, for example, 1-propynyl, 1-butynyl, 3-butynyl, 1-pentynyl, 3-pentynyl, 3-methyl-3-butynyl, 1-hexynyl, 3-hexynyl, 3-hexynyl, 3-heptynyl, 1-octynyl, 1-nonynyl, 1-decynyl, 1-undecynyl, 1-dodecynyl, and the like.

The term "alkylene" as used herein refers to a divalent group derived from a straight or branched chain saturated hydrocarbon having from 1 to 10 carbon atoms by the removal of two hydrogen atoms, for example methylene, 1,2-ethylene, 1,1-ethylene, 1,3-propylene, 2,2-dimethylpropylene, and the like. The alkylene groups of this invention can be optionally substituted. The alkylene group can also be substituted with one or more of the substituents selected from lower alkyl, lower alkoxy, lower thioalkoxy, —O(CH$_2$)$_{0-2}$CF$_3$, halogen, nitro, cyano, =O, =S, —OH, —SH, —CF$_3$, —CO$_2$H, —CO$_2$C$_1$–C$_6$ alkyl, —NH$_2$, —NHC$_1$–C$_6$ alkyl, —CONR'R", or —N(C$_1$–C$_6$alkyl)$_2$ where R' and R" are independently alkyl, akenyl, alkynyl, aryl, or joined together to form a 4 to 7 member ring. Useful alkylene groups have from 1 to 6 carbon atoms (C$_1$–C$_6$ alkylene).

The term "halogen" includes chlorine, fluorine, bromine, and iodine.

The term "heteroatom" as used herein represents oxygen, nitrogen, or sulfur (O, N, or S) as well as sulfoxyl or sulfonyl (SO or SO$_2$) unless otherwise indicated.

The term "heteroalkyl" as used herein, refers to an alkyl group that includes one or more heteroatoms such as oxygen, sulfur, or nitrogen (with valence completed by hydrogen or oxygen) in the carbon chain or terminating the carbon chain.

The term "hydrocarbon chain" as used herein refers to a straight hydrocarbon of from 2 to 6 carbon atoms. The hydrocarbon chain is optionally substituted with one or more substituents selected from lower alkyl, lower alkoxy, lower thioalkoxy, —O(CH$_2$)$_{0-2}$CF$_3$, halogen, nitro, cyano, =O, =S, —OH, —SH, —CF$_3$, —CO$_2$H, —CO$_2$C$_1$–C$_6$ alkyl, —NH$_2$, —NHC$_1$–C$_6$ alkyl, —CONR'R", or —N(C$_1$–C$_6$alkyl)$_2$ where R' and R" are independently alkyl, akenyl, alkynyl, aryl, or joined together to form a 4 to 7 member ring.

The term "hydrocarbon-heteroatom chain" as used herein refers to a hydrocarbon chain wherein one or more carbon atoms are replaced with a heteroatom. The hydrocarbon-heteroatom chain is optionally substituted with one or more substituents selected from lower alkyl, lower alkoxy, lower thioalkoxy, —O(CH$_2$)$_{0-2}$CF$_3$, halogen, nitro, cyano, =O, =S, —OH, —SH, —CF$_3$, —CO$_2$H, —CO$_2$C$_1$–C$_6$ alkyl, —NH$_2$, —NHC$_1$–C$_6$ alkyl, —CONR'R", or —N(C$_1$–C$_6$alkyl)$_2$ where R' and R" are independently alkyl, akenyl, alkynyl, aryl, or joined together to form a 4 to 7 member ring.

The term "heteroalkylene" as used herein, refers to an alkylene radical as defined above that includes one or more heteroatoms such as oxygen, sulfur, or nitrogen (with valence completed by hydrogen or oxygen) in the carbon chain or terminating the carbon chain.

The terms "lower alkoxy" and "lower thioalkoxy" as used herein refers to O-alkyl or S-alkyl of from 1 to 6 carbon atoms as defined above for "lower alkyl."

The term "haloalkyl" as used herein refers to a lower alkyl radical, as defined above, bearing at least one halogen substituent, for example, chloromethyl, fluoroethyl, or trifluoromethyl, and the like. Haloalkyl can also include perfluoroalkyl wherein all hydrogens of a loweralkyl group are replaced with fluorides.

The term "aryl" as used herein refers to an aromatic ring which is unsubstituted or optionally substituted by 1 to 4 substituents selected from lower alkyl, lower alkoxy, lower thioalkoxy, halogen, nitro, cyano —OH, —SH, —CF$_3$, —CO$_2$H, —CO$_2$C$_1$–C$_6$ alkyl, —NH$_2$, —NHC$_1$–C$_6$ alkyl, —SO$_2$alkyl, —SO$_2$NH$_2$, —CONR'R", or —N(C$_1$–C$_6$alkyl)$_2$, where R' and R" are independently alkyl, akenyl, alkynyl, aryl, or joined together to form a 4 to 7 member ring. Examples include, but are not limited to phenyl, 2-chlorophenyl, 3-chlorophenyl, 4-chlorophenyl, 2-methylphenyl, 3-methylphenyl, 4-methylphenyl, 2-methoxyphenyl, 3-methoxyphenyl, 4-methoxyphenyl, 2-chloro-3-methylphenyl, 2-chloro-4-methylphenyl, 2-chloro-5-methylphenyl, 3-chloro-2-methylphenyl, 3-chloro-4-methylphenyl, 4-chloro-2-methylphenyl, 4-chloro-3-methylphenyl, 5-chloro-2-methylphenyl, 2,3-dichlorophenyl, 2,5-dichlorophenyl, 3,4-dichlorophenyl, 2,3-dimethylphenyl, 3,4-dimethylphenyl, and the like.

The term "arylene" as used herein refers to a divalent group derived from an aromatic ring. The arylene group can also be substituted with one or more of the substituents listed above for aryl.

The term "heteroaryl" means an aromatic ring containing one or more heteroatoms. The heteroaryl is optionally substituted with one or more groups enumerated for aryl. Examples of heteroaryl include, but are not limited to thienyl, furanyl, pyrrolyl, pyridyl, pyrimidyl, imidazoyl, pyrazinyl, oxazolyl, thiazolyl, benzothienyl, benzofuranyl, indolyl, quinolinyl, isoquinolinyl, and quinazolinyl, and the like.

The term "cycloalkylene" as used herein refers to a divalent group derived from a cyclic saturated hydrocarbon having from 3 to 8 carbon atoms by the removal of two hydrogen atoms. The cycloalkylene groups of this invention can be optionally substituted. The alkylene group can also be substituted with one or more of the substituents selected from lower alkyl, lower alkoxy, lower thioalkoxy, —O(CH$_2$)$_{0-2}$CF$_3$, halogen, nitro, cyano, =O, =S, —OH, —SH, —CF$_3$, —OCF$_3$, —CO$_2$H, —CO$_2$C$_1$-C$_6$ alkyl, —NH$_2$, —NHC$_1$-C$_6$ alkyl, —CONR'R", or —N(C$_1$-C$_6$alkyl)$_2$ where R' and R" are independently alkyl, akenyl, alkynyl, aryl, or joined together to form a 4 to 7 member ring. Useful cycloalkylene groups have from 3 to 6 carbon atoms (C$_3$-C$_6$ alkyl).

The term "heterocycloalkylene" as used herein, refers to a cycloalkylene group that includes one or more heteroatoms such as oxygen, sulfur, or nitrogen (with valence completed by hydrogen or oxygen) in the carbon chain or terminating the carbon chain.

The term "heterocycle" means a saturated or unsaturated mono- or polycyclic (i.e. bicyclic) ring incorporating one or more (i.e. 1–4) heteroatoms selected from N, O, and S. It is understood that a heterocycle is optionally substituted with —OH, —O(alkyl), SH, S(alkyl), amine, halogen, acid, ester, amide, amidine, alkyl ketone, aldehyde, nitrile, haloalkyl, nitro, sulphone, sulfoxide or C$_1$-C$_6$ alkyl. Examples of suitable monocyclic heterocycles include, but are not limited to substituted or unsubstituted thienyl, furanyl, pyrrolyl, imidazolyl, pyrazolyl, thiazolyl, isothiazolyl, oxazolyl, isoxazolyl, triazoiyl, tetrazolyl, pyridinyl, pyrazinyl, pyrimidinyl, piperidinyl, pyrrolidinyl, piperazinyl, azetidinyl, aziridinyl, morpholinyl, thietanyl, oxetaryl. Examples of monocyclic heterocycles include, but are not limited to, 1-, 2-, 4-, or 5-imidazolyl, 1-, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 1, 3-, or 5-triazolyl, 1-, 2-, or 3-tetrazolyl, 2-pyrazinyl, 2-, 4-, or 5-pyrimidinyl, 1- or 2-piperazinyl, 2-, 3-, or 4-morpholinyl. Examples of suitable bicyclic heterocycles include, but are not limited to indolizinyl, isoindolyl, benzofuranyl, benzothienyl, benzoxazolyl, benzimidazolyl, quinolinyl, isoquinolinyl, quinazolinyl, 1-, 2-, 3-, 4-, 5-, 6-, or 7-indolyl, 1-, 2-, 3-, 5-, 6-, 7-, or 8-indolizinyl, 1-, 2-, 3-, 4-, 5-, 6-, or 7-isoindolyl, 2-, 3-, 4-, 5-, 6-, or 7-benzothienyl, 2-, 4-, 5-, 6-, or 7-benzoxazolyl, 1-, 2-, 4-, 5-, 6-, or 7-benzimidazolyl, 2-, 3-, 4-, 5-, 6-, 7-, or 8-quinolinyl, and 1-, 3-, 4-, 5-, 6-, 7-, or 8-isoquinolinyl.

The term "cycloalkenyl" means a cycloalkyl group having one or more carbon-carbon double bonds. Example includes cyclobutene, cyclopentene, cyclohexene, cycloheptene, cyclobutadiene, cyclopentadiene, and the like.

The term "heterocycloalkyl" means a nonaromatic ring with from 4 to 8 members, with up to 4 heteroatoms for example, N, O, and S. Examples of heterocycloalkyl, include but are not limited to, 2- or 3-tetrahydrothieno, 2- or 3-tetrahydrofurano, 2- or 3-pyrrolidino, 2-, 4-, or 5-thiazolidino, 2-, 4-, or 5-oxazolidino, 2-, 3-, or 4-piperidino, N-morpholinyl or N-thiamorpholinyl or tetrahydropyrano.

The term "cycloalkyl" means a saturated hydrocarbon ring, and includes for example, cyclopropyl, cyclobutyl, cyclopentyl, cyclohexyl, cycloheptyl, and cyclooctyl, and the like. The cycloalkyl group is optionally substituted with 1 to 3 substituents from the group of substituents described above for aryl. Useful cycloalkyl include those having from 3 to 8 carbon atoms.

The term "patient" means all mammals including humans. Examples of patients include humans, cows, dogs, cats, goats, sheep, pigs, and rabbits.

A "therapeutically effective amount" is an amount of a compound of the present invention that when administered to a patient ameliorates a symptom of dyslipidemia, non-insulin dependent diabetes mellitus, obesity, hyperglycemia, hypercholesteremia, hyperlipidemia, atherosclerosis, hypertriglyceridemia, or hyperinsulinemia.

The term "a pharmaceutically acceptable salt" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, and laurylsulphonate salts, and the like. These also include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," *J. Pharm. Sci.*, 1977;66:1–19, which is incorporated herein by reference.) The free base form may be regenerated by contacting the salt form with a base. While the free base may differ from the salt form in terms of physical properties, such as solubility, the salts are equivalent to their respective free bases for the purposes of the present invention.

The present invention provides compounds capable of altering PPAR activity having Formula I:

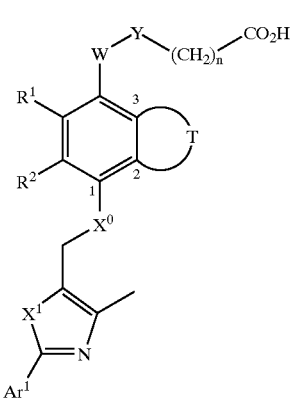

or a pharmaceutically acceptable salt thereof,
where:

T is a saturated or unsaturated, substituted or unsubstituted hydrocarbon chain or hydrocarbon-heteroatom chain having from 3 to 6 atoms wherein the carbon atom of position 2 is connected to the carbon atom of position 3 to form a five to eight member ring;

W is O, S, $CH_2$, $CR^4R^5$, $NR^3$, cycloalkylene, or heterocycloalkylene;

Y is absent, O, or $CR^4R^5$ wherein

Y is $CR^4R^5$ or absent when W is O, S, or $NR^3$; and

Y is O or absent when W is $CH_2$ or $CR^4R^5$;

$R^1$ and $R^2$ are independently hydrogen, lower alkyl, lower alkoxy, haloalkyl, $-O-(CH_2)_pCF_3$, halogen, nitro, cyano, $-OH$, $-SH$, $-CF_3$, $-S(O)_p$alkyl, $S(O)_p$aryl, $-(CH_2)_m OR^3$, $-(CH_2)_m NR^6R^7$, $-COR^3$, $-CO_2H$, $-CO_2R^3$, or $-NR^6R^7$;

$R^3$ is hydrogen, alkyl, alkenyl, alkynyl, or aryl;

$R^4$ and $R^5$ are independently hydrogen, alkyl, alkenyl, alkynyl, or aryl, or joined together to form a 4 to 7 member ring having 0 to 3 heteroatoms;

$R^6$ and $R^7$ are independently hydrogen, alkyl, alkenyl, alkynyl, $-CO$alkyl, $-CO$aryl, cycloalkyl, $-CO_2$alkyl, $-CO_2$aryl, $-SO_2$alkyl, $-SO_2$aryl, or joined together to form a 4 to 7 member ring having 1 to 3 heteroatoms;

$X^0$ and $X^1$ are independently O or S;

$Ar^1$ is substituted or unsubstituted aryl or heteroaryl;

m is 0 to 5;

n is 0 to 5; and p is 0 to 2.

In the present embodiment, T is optionally substituted with 1 or more substituents selected from the group consisting of lower alkyl, lower alkoxy, lower thioalkoxy, $-O(CH_2)_{0-2}CF_3$, halogen, nitro, cyano, $=O$, $=S$, $-OH$, $-SH$, $-CF_3$, $-CO_2H$, $-CO_2C_1-C_6$ alkyl, $-NH_2$, $-NHC_1-C_6$ alkyl, $-OCH_2O-$, and $-N(C_1-C_6\text{alkyl})_2$.

Examples of T include, but are not limited to, $-CH_2CH_2CO-O-$, $-CH_2-CH_2-O-CO-$, $-CH_2-CH_2-CH_2-CH_2-$, $-HC=CH-HC=CH-$, $-N=CH-HC=CH-$, $-HC=N-HC=CH-$, $-HC=CH-N=CH-$, $-HC=CH-HC=N-$, $-CH_2-CH_2-CH_2-$, $-CH_2-CH_2-O-CH_2-$, $-CH_2-HC=CH-CH_2-$, $-CH_2-HC=CH-$, $-CH_2CH_2-NH-CH_2-$, $-COCH=CH-O-$, $-O-CH=CH-CO-$, $-CH=CH-NR^4-$, $-NR^4-CH=CH-$, $-CH=CH-CH_2-$, $-CH_2-CH_2-NR^4-$, $-NR^4-CH_2-CH_2-$, $-O-CH_2-CH_2-$, $-CH_2-CH_2-O-$, $-CH_2-CH_2-CO-$, $-CH_2-CO-CH_2-$, $-CO-CH_2-CH_2-$, $-CH_2-CH_2-CH_2-CO-$, $-CO-CH_2-CH_2-CH_2-$, $-CH_2-CO-CH_2-CH_2-$, $-CH_2-CH_2-CO-CH_2-$, $-CH_2-CH_2-CH_2-NR^4-$, $-NR^4-CH_2-CH_2-CH_2-$, $-O-CH_2-CH_2-CH_2-$, $-CH_2-CH_2-CH_2-O-$, $-CO-NR^4-CH_2-CH_2-$, $NR^4CO-CH_2-CH_2-$, $-CH_2-CH_2-NR^4-CO-$, and $-CH_2-CH_2-CO-NR^4-$. It will be understood that the left-most atom of these groups in attached to the atom labeled "3" in Formula I and the right-most atom of these groups is attached to the atom label "2" in Formula I.

Examples of compounds of Formula I include those where W is O, Y is absent, and n is 1.

Additional Examples of compounds of Formula I include those where $R^1$ and $R^2$ are independently hydrogen, alkyl, or alkoxy. Examples of compounds of Formula I where $R^1$ and $R^2$ are independently alkyl include, but are not limited to, those where $R^1$ and $R^2$ are independently methyl, ethyl, isopropyl, n-propyl, t-butyl, n-butyl, or isobutyl. Examples of compounds of Formula I where $R^1$ and $R^2$ are independently alkoxy include, but are not limited to, those where $R^1$ and $R^2$ are independently methoxy, ethoxy, isopropoxy, n-propoxy, t-butoxy, n-butoxy, or isobutoxy.

Additional Examples of compounds of Formula I include those where $R^1$ is hydrogen and $R^2$ is alkyl, or alkoxy. Examples of compounds of Formula I where $R^1$ is hydrogen and $R^2$ is alkyl or alkoxy include, but are not limited to, those where $R^2$ is methoxy, ethoxy, isopropoxy, n-propoxy, t-butoxy, n-butoxy, isobutoxy, methyl, ethyl, isopropyl, n-propyl, t-butyl, n-butyl, or isobutyl.

In yet another example of compounds of the present invention, T in Formula I is $-Y^4=Y^3-Y^2=Y^1-$, $Y^4-Y^3-Y^2-Y^1-$, $-Y^4=Y^3-Y^2-Y^1-$, $-Y^4-Y^3-Y^2=Y^1-$, or $Y^4-Y^3=Y^2-Y^1-$. Examples of compounds of the invention where T in Formula I is $-Y^4=Y^3-Y^2=Y^1-$, $-Y^4-Y^3-Y^2-Y^1-$, $-Y^4=Y^3-Y^2-Y^1-$, $-Y^4-Y^3-Y^2=Y^1-$, or $Y^4-Y^3=Y^2-Y^1-$ include, but are not limited to compounds of Formula IIa, Formula IIb, Formula IIc, Formula IId, and Formula IIe:

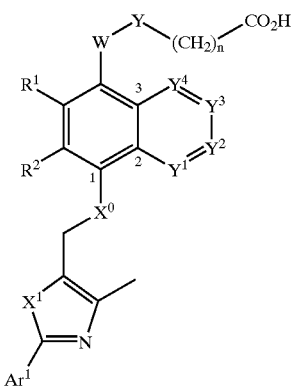

IIa

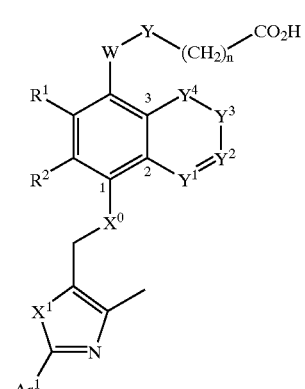

IIb

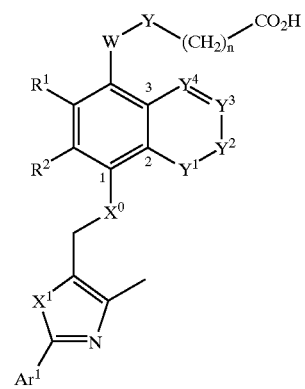

IIc

-continued

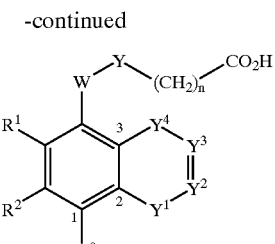

IId

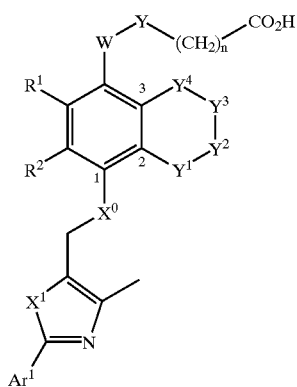

IIe or a pharmaceutically acceptable salt thereof, where: W, Y, $R^1$, $R^2$, $R^4$, $R^5$, $R^6$, $R^7$, $X^0$, $X^1$, $Ar^1$, m, n, and p are the same as defined above for Formula I; and $Y^1$, $Y^2$, $Y^3$ and $Y^4$ are each independently a carbon atom or a heteroatom wherein the carbon atom and the heteroatom are bonded to a sufficient number of hydrogen atoms or substituents as listed above for T to complete the valency of each atom with the proviso that $Y^1$, $Y^2$, $Y^3$ and $Y^4$ are not all heteroatoms and that not more than two adjacent atoms in $Y^1$, $Y^2$, $Y^3$ and $Y^4$ are heteroatoms and that in Formulae IIb, IIc, and IId, $Y^1$, $Y^2$, $Y^3$ and $Y^4$ are not all carbon.

Examples of compounds of Formula II, Formula IIa, Formula IIb, Formula IIc, Formula IId and Formula IIe, include those where W is O, Y is absent, and n is 1.

Additional Examples of compounds of Formula II, Formula IIa, Formula IIb, Formula IIc, Formula IId and Formula IIe include those where $R^1$ and $R^2$ are independently hydrogen, alkyl, or alkoxy. Examples of compounds of Formula I where $R^1$ and $R^2$ are independently alkyl include, but are not limited to, those where $R^1$ and $R^2$ are independently methyl, ethyl, isopropyl, n-propyl, t-butyl, n-butyl, or isobutyl. Examples of compounds of Formula I where $R^1$ and $R^2$ are independently alkoxy include, but are not limited to, those where $R^1$ and $R^2$ are independently methoxy, ethoxy, isopropoxy, n-propoxy, t-butoxy, n-butoxy, or isobutoxy.

Additional Examples of compounds of Formula II, Formula IIa, Formula IIb, Formula IIc, Formula IId and Formula IIe include those where $R^1$ is hydrogen and $R^2$ is alkyl, or alkoxy. Examples of compounds of Formula II, Formula IIa, Formula IIb, Formula IIc, Formula IId and Formula IIe where $R^1$ is hydrogen and $R^2$ is alkyl or alkoxy include, but are not limited to, those where $R^2$ is methoxy, ethoxy, isopropoxy, n-propoxy, t-butoxy, n-butoxy, isobutoxy, methyl, ethyl, isopropyl, n-propyl, t-butyl, n-butyl, or isobutyl.

In yet another example of compounds of the present invention, T in Formula I is $-Z^3=Z^2-Z^1-$, $-Z^3-Z^2=Z^1$, or $-Z^3-Z^2-Z^1-$. Examples of compounds of the present invention where T in Formula I is $-Z^3=Z^2-Z^1-$, $-Z^3-Z^2=Z^1$, or $-Z^3-Z^2-Z^1-$ include, but are not limited to, compounds of Formula IIIa, Formula IIIb, and Formula IIIc:

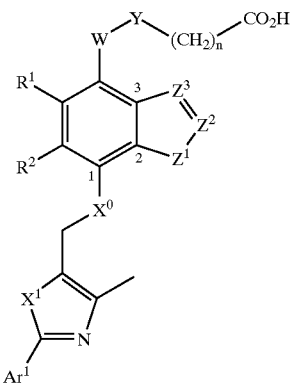

IIIa

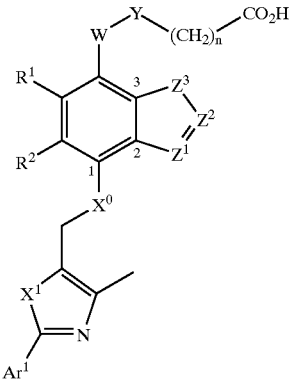

IIIb

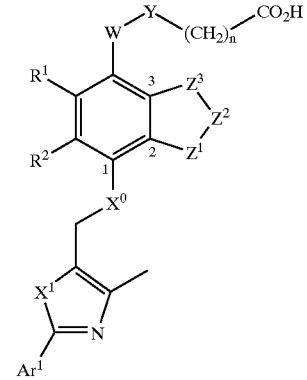

IIIc or a pharmaceutically acceptable salt thereof, where: W, S, $R^1$, $R^2$, $R^3$, $R^4$, $R^5$, $R^6$, $R^7$, $Ar^1$, $X^0$, $X^1$, m, n, and p are the same are provided above for Formula I; and $Z^1$, $Z^2$, and $Z^3$ are each independently a carbon atom or a heteroatom wherein the carbon atom and the heteroatom are bonded to a sufficient number of hydrogen atoms or substituents as listed above for T to complete the valency of each atom with the proviso that in Formulae IIIa and IIIb $Z^1$, $Z^2$, and $Z^3$ are not all heteroatoms. In an Example of compounds of Formula IIIc, $Z^1$, $Z^2$, and $Z^3$ are all carbon atoms.

Examples of compounds of Formula III, Formula IIIa, Formula IIIb, and Formula IIIc, include those where W is O, Y is absent, and n is 1.

Additional Examples of compounds of Formula III, Formula IIIa, Formula IIIb, and Formula IIIc include those where $R^1$ and $R^2$ are independently hydrogen, alkyl, or alkoxy. Examples of compounds of Formula I where $R^1$ and $R^2$ are independently alkyl include, but are not limited to, those where $R^1$ and $R^2$ are independently methyl, ethyl, isopropyl, n-propyl, t-butyl, n-butyl, or isobutyl. Examples of compounds of Formula I where $R^1$ and $R^2$ are independently alkoxy include, but are not limited to, those where $R^1$ and $R^2$ are independently methoxy, ethoxy, isopropoxy, n-propoxy, t-butoxy, n-butoxy, or isobutoxy.

Additional Examples of compounds of Formula III, Formula IIIa, Formula IIIb, and Formula IIIc include those where $R^1$ is hydrogen and $R^2$ is alkyl, or alkoxy. Examples of compounds of Formula II, Formula IIa, Formula IIb, Formula IIc, Formula IId and Formula IIe where $R^1$ is hydrogen and $R^2$ is alkyl or alkoxy include, but are not limited to, those where $R^2$ is methoxy, ethoxy, isopropoxy, n-propoxy, t-butoxy, n-butoxy, isobutoxy, methyl, ethyl, isopropyl, n-propyl, t-butyl, n-butyl, or isobutyl.

Examples of compounds of Formula I include
{4-[4-Methyl-2-(4-trifluoromethyl-phenyl)-thiazol-5-ylmethylsulfanyl]-5-oxo-5,6,7,8-tetrahydro-naphthalen-1-yloxy}-acetic acid;
{4-[4-Methyl-2-(4-trifluoromethyl-phenyl)-thiazol-5-ylmethylsulfanyl]-8-oxo-5,6,7,8-tetrahydro-naphthalen-1-yloxy}-acetic acid;
{4-[4-Methyl-2-(4-trifluoromethyl-phenyl)-thiazol-5-ylmethylsulfanyl]-7-oxo-5,6,7,8-tetrahydro-naphthalen-1-yloxy}-acetic acid;
{4-[4-Methyl-2-(4-trifluoromethyl-phenyl)-thiazol-5-ylmethylsulfanyl]-6-oxo-5,6,7,8-tetrahydro-naphthalen-1-yloxy}-acetic acid;
{5-[4-Methyl-2-(4-trifluoromethyl-phenyl)-thiazol-5-ylmethylsulfanyl]-4-oxo-4H-chromen-8-yloxy}-acetic acid;
{8-[4-Methyl-2-(4-trifluoromethyl-phenyl)-thiazol-5-ylmethylsulfanyl]-4-oxo-4H-chromen-5-yloxy}-acetic acid;
{8-[4-Methyl-2-(4-trifluoromethyl-phenyl)-thiazol-5-ylmethylsulfanyl]-4-oxo-chroman-5-yloxy}-acetic acid;
{5-[4-Methyl-2-(4-trifluoromethyl-phenyl)-thiazol-5-ylmethylsulfanyl]-4-oxo-chroman-8-yloxy}-acetic acid;
{8-[4-Methyl-2-(4-trifluoromethyl-phenyl)-thiazol-5-ylmethylsulfanyl]-quinolin-5-yloxy}-acetic acid;
{8-[4-Methyl-2-(4-trifluoromethyl-phenyl)-thiazol-5-ylmethylsulfanyl]-isoquinolin-5-yloxy}-acetic acid;
{1-Methyl-7-[4-methyl-2-(4-trifluoromethyl-phenyl)-thiazol-5-ylmethylsulfanyl]-1H-benzoimidazol-4-yloxy}-acetic acid;
{3-Methyl-7-[4-methyl-2-(4-trifluoromethyl-phenyl)-thiazol-5-ylmethylsulfanyl]-1H-benzoimidazol-4-yloxy}-acetic acid;
{7-[4-Methyl-2-(4-trifluoromethyl-phenyl)-thiazol-5-ylmethylsulfanyl]-1H-indol-4-yloxy}-acetic acid;
{1-Methyl-7-[4-methyl-2-(4-trifluoromethyl-phenyl)-thiazol-5-ylmethylsulfanyl]-1H-indol-4-yloxy}-acetic acid;
{7-[4-Methyl-2-(4-trifluoromethyl-phenyl)-thiazol-5-ylmethylsulfanyl]-benzo[b]thiophen-4-yloxy}-acetic acid;
{7-[4-Methyl-2-(4-trifluoromethyl-phenyl)-thiazol-5-ylmethylsulfanyl]-benzofuran-4-yloxy}-acetic acid; and
pharmaceutically acceptable salts thereof.

Additional examples of compounds of Formula I include
{8-[4-Methyl-2-(4-trifluoromethyl-phenyl)-thiazol-5-ylmethylsulfanyl]-chroman-5-yloxy}-acetic acid;
{4-[4-Methyl-2-(4-trifluoromethyl-phenyl)-thiazol-5-ylmethylsulfanyl]-5,6,7,8-tetrahydro-naphthalen-1-yloxy}-acetic acid;
{4-[4-Methyl-2-(4-trifluoromethyl-phenyl)-thiazol-5-ylmethylsulfanyl]-naphthalen-1-yloxy}-acetic acid;
2-[6-methyl-8-({4-methyl-2-[4-(trifluoromethyl)phenyl](1,3-thiazol-5-yl)}methylthio)chroman-5-yloxy]acetic acid;
2-[5-methyl-7-({4-methyl-2-[4-(trifluoromethyl)phenyl](1,3-thiazol-5-yl)}methylthio)-2,3-dihydrobenzo[b]furan-4-yloxy]acetic acid;
{5-Methyl-7-[4-methyl-2-(4-trifluoromethyl-phenyl)-thiazol-5-ylmethylsulfanyl]-indan-4-yloxy}-acetic acid; and
pharmaceutically acceptable salts thereof.

A Further example of a compound of Formula I includes
{7-[4-Methyl-2-(4-trifluoromethyl-phenyl)-thiazol-5-ylmethylsulfanyl]-indan-4-yloxy}-acetic acid; and
pharmaceutically acceptable salts thereof.

Certain of the compounds of the present invention possess one or more chiral centers and each center may exist in the R or S configuration. The present invention includes all diastereomeric, enantiomeric, and epimeric forms as well as the appropriate mixtures thereof. Stereoisomers may be obtained, if desired, by methods known in the art as, for example, the separation of stereoisomers by chiral chromatographic columns. Additionally, the compounds of the present invention may exist as geometric isomers. The present invention includes all cis, trans, syn, anti, entgegen (E), and zusammen (Z) isomers as well as the appropriate mixtures thereof.

In some situations, compounds may exist as tautomers. All tautomers are included within Formulae I-III and are provided by this invention.

The present invention includes all pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention are suitable to be administered to a patient for the treatment, control, or prevention of non-insulin dependent diabetes mellitus, hypercholesteremia, hyperlipidemia, obesity, hyperglycemia, hyperlipidemia, atherosclerosis, hypertriglyceridemia, and hyperinsulinemia. Accordingly, the compounds may be administered to a patient alone or as part of a composition that contains other components such as excipients, diluents, and carriers, all of which are well-known in the art. The compositions can be administered to humans and/or animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar, as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 2,000 mg per day. For a normal human adult having a body weight of about 70 kilograms, a dosage in the range of about 0.01 to about 10 mg per kilogram of body weight per day is preferable. However, the specific dosage used can vary. For example, the dosage can depend on a numbers of factors including the requirements of the patient, the severity of the condition being treated, and the pharmacological activity of the compound being used. The determination of optimum dosages for a particular patient is well-known to those skilled in the art.

Preparation of Compounds of the Invention

The present invention contains compounds that can be synthesized in a number of ways familiar to one skilled in organic synthesis. The compounds outlined herein can be synthesized according to the methods described below, along with methods typically utilized by a synthetic chemist, and combinations or variations of those methods which are generally known to one skilled in the art of synthetic chemistry. The synthetic route of compounds in the present invention is not limited to the methods outlined below. It is assumed one skilled in the art will be able to use the schemes outlined below to synthesize compounds claimed in this invention. Individual compounds may require manipulation of the conditions in order to accommodate various functional groups. A variety of protecting groups generally known to one skilled in the art may be required. Purification, if necessary, can be accomplished on a silica gel column eluted with the appropriate organic solvent system. Also, reverse phase HPLC or recrystallization may be employed if needed.

In still another embodiment of the present invention, a method of preparing the compounds of Formula I–III is provided. The compounds of Formulae I–III can be prepared by reacting:

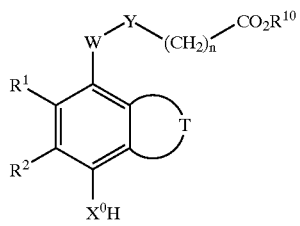

in a solvent in the presence of a base such as cesium carbonate with the aryl halide:

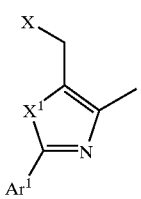

wherein

T, $R^1$, $R^2$, $R^3$, $R^4$, $R^5$, $R^6$, $R^7$, $X^0$, $X^1$, $Ar^1$, W, Y m, n, and p are the same as described above;

X is a halogen; and $R^{10}$ is a lower alkyl.

The resulting ester is then converted to the compounds of Formulae I–III by various methods known in the art for the conversion of esters to acids, such as via hydrolysis for example. A useful aryl halide, for example, is 5-chloromethyl-4-methyl-2-(4-trifluoromethyl-phenyl)-thiazole. The synthetic route to compounds with Formula IIa-e is provided when T is —$Y^4$═$Y^3$—$Y^2$═$Y^1$—, —$Y^4$═$Y^3$—$Y^2$—$Y^1$—, —$Y^4$═$Y^3$—$Y^2$—$Y^2$—$Y^1$—, —$Y^4$—$Y^3$—$Y^2$═$Y^1$, or —$Y^4$—$Y^3$═$Y^2$—$Y^1$— as defined above. The preparation of compounds with Formula IIIa–c is provided when T is -$Z^3$═$Z^2$-$Z^1$-, -$Z^3$-$Z^2$═$Z^1$-, or -$Z^3$-$Z^2$-$Z^1$- as defined above.

The compounds of the present invention can be made by the methods described in Schemes 1–3 for example. Scheme I provides an alternative preparation for compounds of the present invention. With reference to Scheme 1, compounds of the general formula A are reacted with trimethylsilyl isothiocyanate and phenyliodine(III) bis(trifluoroacetate) to form compounds of the general formula B. Compounds of the general formula C are then prepared by reduction of B with dithiothreitol in methanol. Compounds of the general formula C are then alkylated with the halide compound D to form compound E. A useful aryl halide compound D, for example, is 5-chloromethyl-4-methyl-2-(4-trifluoromethyl-phenyl)-thiazole. Compounds of the general formula E are then saponified with LiOH in the THF to give the final compound F. Compound F corresponds to the compounds of the present invention described by Formula I. The synthetic route to compounds with Formula IIa-e is provided when T is —$Y^4$═$Y^3$—$Y^2$═$Y^1$—, —$Y^4$—$Y^3$—$Y^2$—$Y^1$—, —$Y^4$═$Y^3$—$Y^2$—$Y^1$—, —$Y^4$—$Y^3$—$Y^2$═$Y^1$—, or —$Y^4$—$Y^3$═$Y^2$—$Y^1$—as defined above. The preparation of compounds with Formula IIIa–c is provided when T is -$Z^3$═$Z^2$-$Z^1$-, -$Z^3$-$Z^2$═$Z^1$-, or -$Z^3$-$Z^2$-$Z^1$- as defined above.

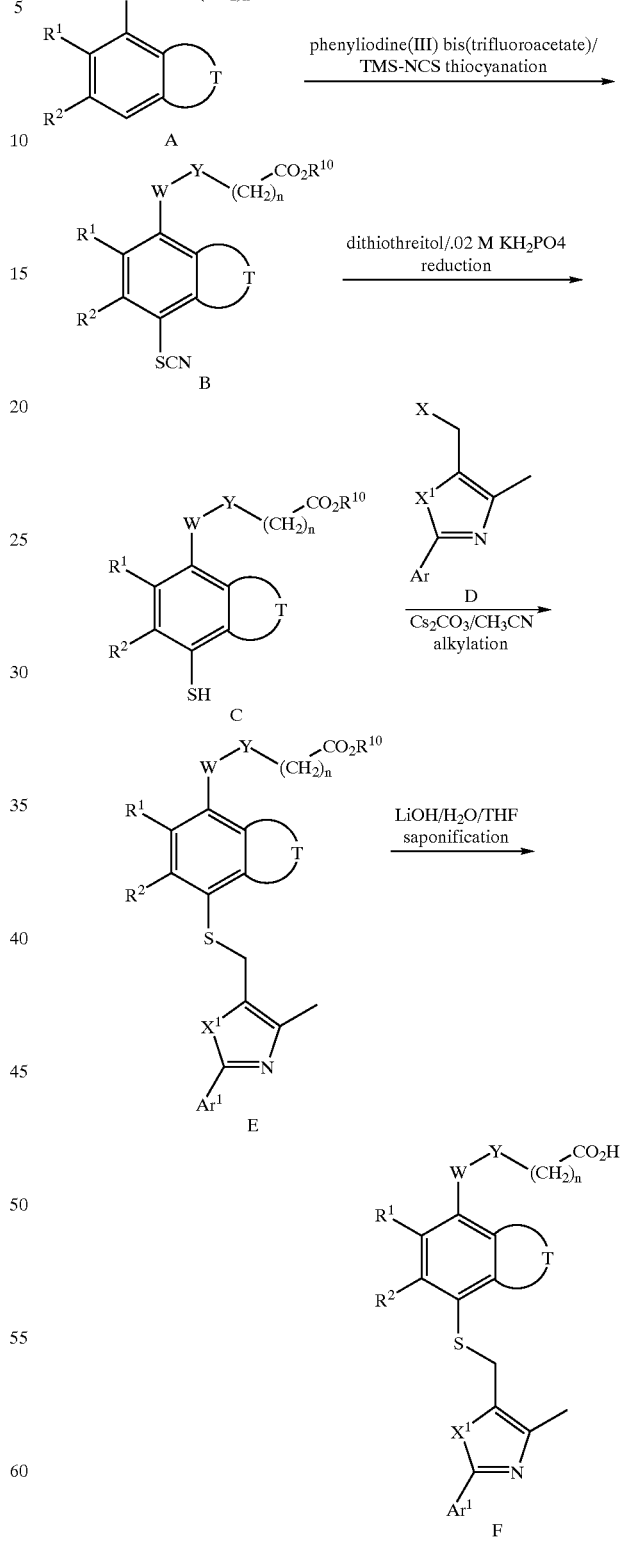

Scheme 1

Scheme 2 provides a synthetic route to compound A in Scheme 1 when W is O, Y is absent, $R^{10}$ is methyl, and n is 1. With reference to Scheme 2, compounds of the general formula G are then alkylated with methyl bromoacetate to give compounds of the general formula A'.

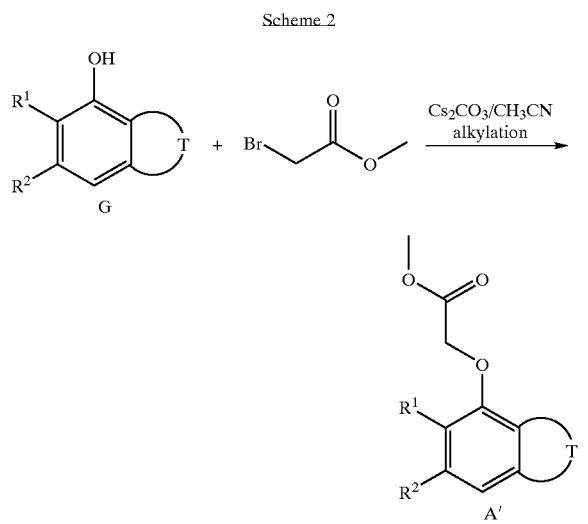

Scheme 3 provides an alternative synthetic route to compound B in Scheme 1 when W is O, Y is absent, $R^{10}$ is methyl, and n is 1. With reference to Scheme 3, compounds of the general formula H are thiocyanated with a mixture of bromine and sodium thiocyanate to give compounds of the general formula J. Compounds of the general formula J can come from commercial sources or syntheses known to those skilled in the art. Compounds of the general formula J are then alkylated with methyl bromoacetate to give compounds of the general formula B.

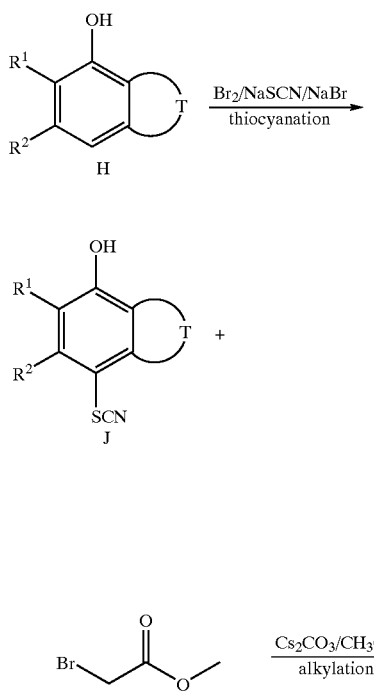

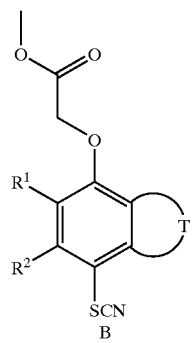

Scheme 4 provides yet another alternative method for preparing the compounds of the present invention. With reference to Scheme 4, compounds of the general formula K are reacted with the potassium triisopropylsilanethiolate and tetrakis(triphenylphosphine) palladium(0) and then reducing the resulting product with cesium fluoride to produce compounds of general formula C. Compounds of the general formula K can come from bromination of the corresponding compound, commercial sources or synthesis' known to those skilled in the art. Compounds of the general formula C are then alkylated with the halide compound D to form compound E. A useful aryl halide compound D, for example, is 5-chloromethyl-4-methyl-2-(4-trifluoromethyl-phenyl)-thiazole. Compounds of the general formula C are then saponified with LiOH in the THF to give the final compound F. Compound F corresponds to the compounds of the present invention described by Formula I. The synthetic route to compounds with Formula IIa-e is provided when T is $-Y^4=Y^3-Y^2=Y^1-$, $-Y^4-Y^3-Y^2-Y^1-$, $-Y^4=Y^3-Y^2-Y^1-$, $-Y^4-Y^3-Y^2=Y^1-$, or $-Y^4-Y^3=Y^2-Y^1-$ as defined above. The preparation of compounds with Formula IIIa-c is provided when T is $-Z^3=Z^2-Z^1-$, $-Z^3-Z^2=Z^1$, or $-Z^3-Z^2-Z^1-$ as defined above.

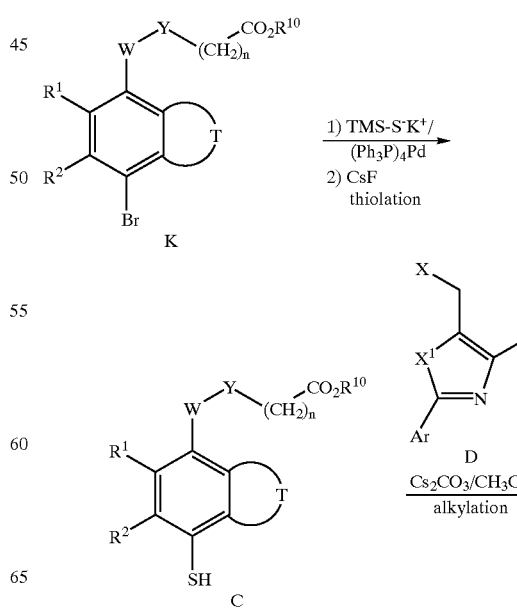

-continued

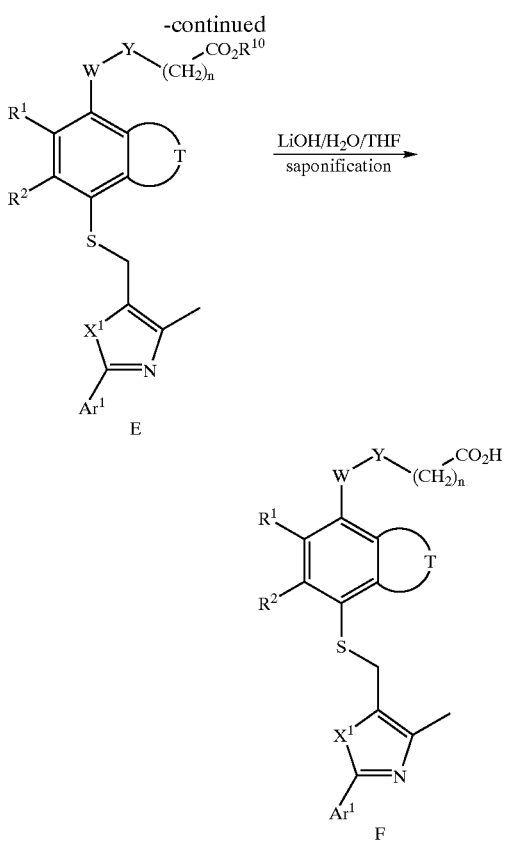

The following non-limiting descriptions also demonstrate methods for the synthesis of compounds of Formulae I–III.

EXAMPLE 1

Synthesis of {8-[4-Methyl-2-(4-trifluoromethyl-phenyl)-thiazol-5-ylmethylsulfanyl]-chroman-5-yloxy}-acetic acid (compound 1)

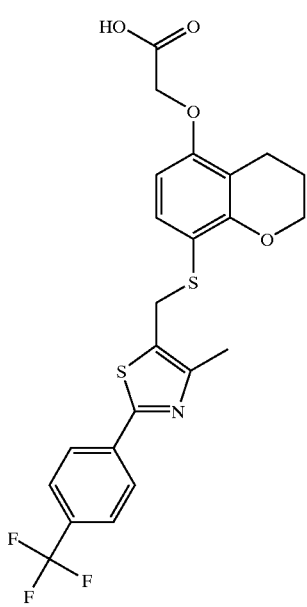

Preparation of Chroman-5-ol (compound 1A)

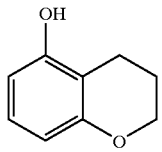

To a solution of 5-hydroxy-chromen-4-one (*J. Het. Chem*, 13, 1976, 211) (2.5 g, 15.4 mmol) and 1 mL HCl(c) in 75 mL de-gassed EtOH/THF (3:1) was added 0.5 g 10% Pd/C. The reaction mixture was stirred at room temperature for 20 h under an atmosphere of 1 atm $H_2$(g). The Pd/C was then filtered off, the filtrate collected and concentrated in vacuo to give 2.1 g (91%) of the title compound pure enough for subsequent use. 400 MHz $^1$H NMR (DMSO-$d_6$) δ 9.27 (s, 1H), 6.76 (t, 1H, J=8.1 Hz), 6.26 (d, 1H, J=8.1 Hz), 6.12 (d, 1H, J=8.1 Hz), 3.98 (t, 2H, J=5.0 Hz), 2.46 (m, 2H), 1.80 (m, 2H).

Preparation of (Chroman-5-yloxy)-acetic acid methyl ester (compound 1B)

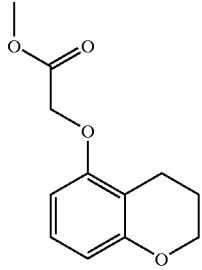

A solution of chroman-5-ol (2.1 g, 14 mmol), methyl bromoacetate (1.6 mL, 16.8 mmol), and cesium carbonate (6.8 g, 21 mmol) in 50 mL acetonitrile was heated at 60° C. for 3 hours. PS-Trisamine scavenger resin was then added to the warmed solution followed by an additional 30 minutes heating. The reaction mixture was then cooled and filtered. The filtrate was collected, diluted with 100 mL ether, washed with brine (1×50 mL), dried ($Na_2SO_4$), and the solvent removed in vacuo to give 2.1 g (68%) of the title compound, pure enough for subsequent use. 400 MHz $^1$H NMR (DMSO-$d_6$) δ 6.92 (t, 1H, J=8.3 Hz), 6.33 (d, 1H, J=8.3 Hz), 6.31 (d, 1H, J=8.3 Hz), 4.72 (s, 2H), 4.02 (t, 2H, J=5.1 Hz), 3.64 (s, 3H), 2.56 (t, 2H, J=6.6 Hz), 1.83 (m, 2H).

Preparation of (8-Thiocyanato-chroman-5-yloxy)-acetic acid methyl ester (compound 1C)

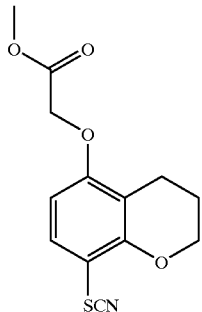

A stirred solution of (chroman-5-yloxy)-acetic acid methyl ester (2.1 g, 9.4 mmol) and trimethylsilyl isothiocyanate (2 mL, 14.1 mmol) in 30 mL 1,1,1,3,3,3-hexafluoropropan-2-ol under a $N_2$ atmosphere was treated with phenyliodine(III) bis(trifluoroacetate). The reaction mixture stirred at room temperature for 1 h and concentrated in vacuo. Purification by flash column chromatography (gradient elution: 10% EtOAc/hexanes to 40% EtOAc/hexanes) gave the title compound (1.3 g, 50%) as a pale yellow solid. 400 MHz $^1$H NMR (DMSO-$d_6$) δ 7.31 (d, 1H, J=8.8 Hz), 6.54 (d, 1H, J=8.8 Hz), 4.83 (s, 2H), 4.21 (t, 2H, J=4.9 Hz), 3.64 (s, 3H), 2.60 (t, 2H, J=6.4 Hz), 1.89 (m, 2H).

Preparation of (8-Mercapto-chroman-5-yloxy)-acetic acid methyl ester (compound 1D)

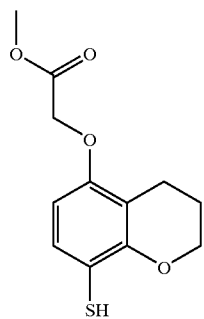

1D

A solution of (8-thiocyanato-chroman-5-yloxy)-acetic acid methyl ester (1.3 g, 4.6 mmol), dithiothreitol (910 mg, 6 mmol), and $KH_2PO_4$ (4.6 mL of a 0.02M solution) in 30 mL MeOH was heated at reflux for 1 hour after which time the reaction was cooled and concentrated in vacuo. Purification by flash column chromatography (gradient elution: 10% EtOAc/hexanes to 35% EtOAc/hexanes) gave the title compound (710 mg, 61%) as a pale yellow solid. 400 MHz $^1$H NMR (DMSO-$d_6$) δ 6.97 (d, 1H, J=8.5 Hz), 6.31 (d, 1H, J=8.5 Hz), 4.70 (s, 2H), 4.40 (s, 1H), 4.11 (t, 2H, J=5.4 Hz), 3.63 (s, 3H), 2.56 (t, 2H, J=6.3 Hz), 1.84 (m, 2H).; MS m/z 255 (M+1).

Preparation of {8-[4-Methyl-2-(4-trifluoromethyl-phenyl)-thiazol-5-ylmethylsulfanyl]-chroman-5-yloxy}-acetic acid methyl ester (compound 1E)

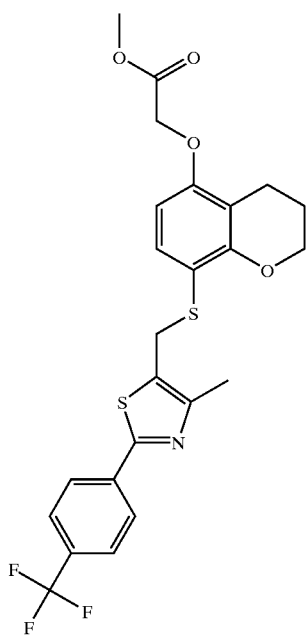

1E

A solution of (8-mercapto-chroman-5-yloxy)-acetic acid methyl ester (410 mg, 1.6 mmol), 5-chloromethyl-4-methyl-2-(4-trifluoromethyl-phenyl)-thiazole (564 mg, 1.9 mmol) and cesium carbonate (787 mg, 2.4 mmol) in 15 ml anhydrous acetonitrile were stirred at 60° C. for 2.5 hours. The reaction was then cooled, filtered and concentrated in vacuo. Purification of the residue by flash column chromatography (gradient elution: 10% EtOAc/hexanes to 35% EtOAc/hexanes) afforded the title compound (95%). IR (thin film) cm$^{-1}$: 1759; 400 MHz $^1$H NMR (DMSO-$d_6$) δ 7.98 (d, 2H, J=8.3 Hz), 7.75 (d, 2H, J=8.3 Hz), 6.96 (d, 1H, J=8.6 Hz), 6.29 (d, 1H, J=8.6 Hz), 4.72 (s, 2H), 4.19 (s, 2H), 4.12 (t, 2H, J=5.1 Hz), 3.61 (s, 3H), 2.56 (t, 2H, J=6.6 Hz), 2.15 (s, 3H), 1.84 (m, 2H).; MS m/z 510 (M+1). Anal. Calc'd for $C_{24}H_{22}F_3N_1O_4S_2$ C, 56.57; H, 4.35; N, 2.75; found: C, 56.45; H, 4.27; N, 2.68.

Preparation of {8-[4-Methyl-2-(4-trifluoromethyl-phenyl)-thiazol-5-ylmethylsulfanyl]-chroman-5-yloxy}-acetic acid (compound 1)

{8-[4-Methyl-2-(4-trifluoromethyl-phenyl)-thiazol-5-ylmethylsulfanyl]-chroman-5-yloxy}-acetic acid methyl ester dissolved in 5 ml THF and 1 ml water, was treated with lithium hydroxide monohydrate (327 mg, 7.8 mmol); stirring at room temperature for 1 hour. The reaction mixture was then acidified to about pH 3 with 2 N HCl. The reaction was then extracted into ethyl acetate (2×20 ml). The organic extracts were washed with brine, dried over anhydrous sodium sulfate, decanted, and concentrated in vacuo. Recrystalization from chloroform/hexanes afforded the title compound (750 mg, 96%) as a pale yellow solid. IR (thin film) cm$^{-1}$: 1745; 400 MHz $^1$H NMR (DMSO-$d_6$) δ 7.98 (d, 2H, J=8.0 Hz), 7.75 (d, 2H, J=8.0 Hz), 6.97 (d, 1H, J=8.5 Hz), 6.27 (d, 1H, J=8.5 Hz), 4.60 (s, 2H), 4.18 (s, 2H), 4.11 (t, 2H, J=4.6 Hz), 2.56 (t, 2H, J=6.6 Hz), 2.15 (s, 3H), 1.83 (m, 2H).; MS m/z 496 (M+1). Anal. Calc'd for $C_{23}H_{20}F_3N_1O_4S_2$ 0.3 $CHCl_3$ C, 52.67; H, 3.85; N, 2.64; found: C, 52.49; H, 3.77; N, 2.54.

EXAMPLE 2

Synthesis of {4-[4-Methyl-2-(4-trifluoromethyl-phenyl)-thiazol-5-ylmethylsulfanyl]-5,6,7,8-tetrahydro-naphthalen-1-yloxy}-acetic acid (compound 2)

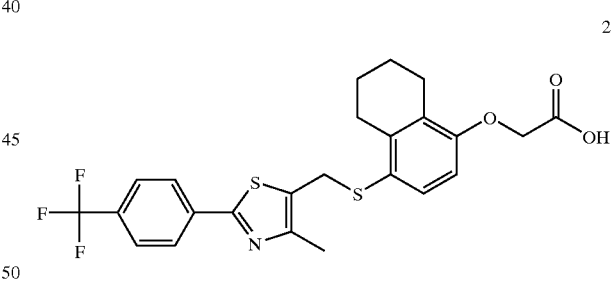

2

Preparation of 4-Thiocyanato-5,6,7,8-tetrahydro-naphthalen-1-ol (compound 2A)

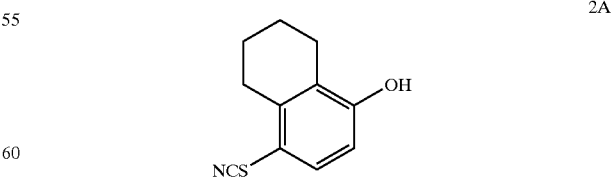

2A 5,6,7,8-Tetrahydro-naphthalen-1-ol (1 g, 6.8 mmol) was dissolved in 25 ml MeOH. Sodium thiocyanate (1.76 g, 22 mmol) and sodium bromide (0.7 g, 6.8 mmol) were added and stirred for 5 minutes at ambient temperature. Bromine (1.2 g, 7.48 mmol) was added drop wise over 5 minutes. The orange solution was allowed to stir two hours. Brine was added and the crude product was extracted twice into ethyl acetate. The combined organic extracts were washed once with brine, dried over anhydrous sodium sulfate, decanted and concentrated. Normal phase chromatography afforded the title product, 1.28 g, 92%. 400 MHz $^1$H NMR (DMSO-$d_6$) δ 11.1 (s, 1H), 7.40 (d, 1H, J=8.8 Hz), 6.61 (d, 1H, 8.8 Hz), 2.78 (m, 2H), 2.59 (m, 2H), 1.70 (m, 4H). MS m/z 278 (m+1)

Preparation of (4-Thiocyanato-5,6,7,8-tetrahydro-naphthalen-1-yloxy)-acetic acid methyl ester (compound 2B)

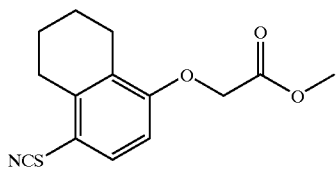

2B

The title compound was prepared in the manner analogous to example 1B utilizing compound 2A. 400 MHz $^1$H NMR (DMSO-$d_6$) δ 7.4 (d, 1H, J=8.8 Hz), 6.80 (d, 1H, 8.8 Hz), 4.84 (s, 2H), 3.64 (s, 3H), 2.78 (m, 2H), 2.59 (m, 2H), 1.70 (m, 4H). MS m/z 278 (m+1).

Preparation of (4-Mercapto-5,6,7,8-tetrahydro-naphthalen-1-yloxy)-acetic acid methyl ester (compound 2C)

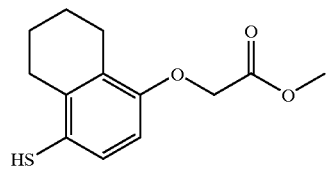

2C

The title compound was prepared in the manner analogous to example 1D utilizing compound 2B. 400 MHz $^1$H NMR (DMSO-$d_6$) δ 7.08 (d, 1H, J=8.8 Hz), 6.55 (d, 1H, 8.8 Hz), 4.71 (s, 1H), 4.70 (s, 2H), 3.63 (s, 3H), 2.45 (m, 2H), 2.44 (m, 2H), 1.65 (m, 4H). MS m/z 253 (M+1).

Preparation of {4-[4-Methyl-2-(4-trifluoromethyl-phenyl)-thiazol-5-ylmethylsulfanyl]-5,6,7,8-tetrahydro-naphthalen-1-yloxy}-acetic acid methyl ester (2D)

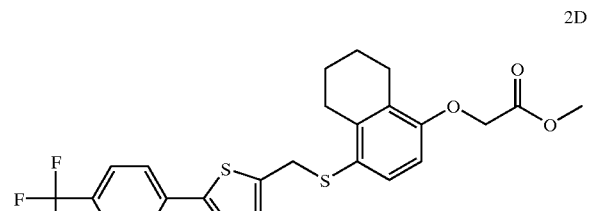

2D

The title compound was prepared in the manner analogous to example 1E utilizing compound 2C. 400 MHz $^1$H NMR (DMSO-$d_6$) δ 7.98 (d, 2H, J=8 Hz), 7.76 (d, 2H, J=8 Hz), 7.11 (d, 1H, J=8.8 Hz), 6.61 (d, 1H, J=8.8 Hz), 4.74 (s, 2H), 4.22 (s, 2H), 3.62 (s, 3H), 2.63 (m, 2H), 2.55 (m, 2H), 1.59 (m, 4H). MS m/z 508 (M+1).

Preparation of {4-[4-Methyl-2-(4-trifluoromethyl-phenyl)-thiazol-5-ylmethylsulfanyl]-5,6,7,8-tetrahydro-naphthalen-1-yloxy}-acetic acid (compound 2)

The title compound was prepared in the manner analogous to example 1 utilizing compound 2D. mp 166–167° C.; IR (thin film) cm$^{-1}$: 2928, 1744, 1711, 1326, 1245, 1118; 400 MHz $^1$H NMR (DMSO-$d_6$) δ 12.93 (br, 1H), 8.00 (d, 2H, J=8 Hz), 7.76 (d, 2H, J=8 Hz), 7.13 (d, 1H, J=8.4 Hz), 6.60 (d, 1H, J=8.4 Hz), 4.62 (s, 2H), 4.22 (s, 2H), 2.63 (m, 2H), 2.54 (m, 2H), 1.58 (m, 4H). MS m/z 494 (M+1). Anal. Calc'd for $C_{24}H_{22}F_3NO_3S_2$ C, 58.40; H, 4.49; N, 2.84; found: C, 58.10; H, 4.38; N, 2.80.

EXAMPLE 3

Synthesis of {4-[4-Methyl-2-(4-trifluoromethyl-phenyl)-thiazol-5-ylmethylsulfanyl]-naphthalen-1-yloxy}-acetic acid (compound 3)

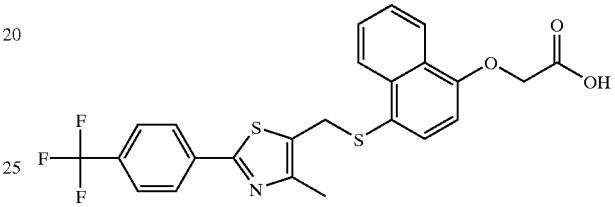

3

Preparation of 4-Thiocyanato-naphthalen-1-ol (compound 3A)

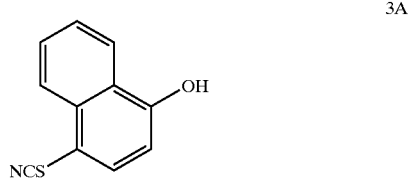

3A

The title compound was prepared in the manner analogous to example 2A. 400 MHz $^1$H NMR (DMSO-$d_6$) δ 11.09 (s, 1H), 8.20 (d, 1H, J=8.4 Hz), 8.17 (d, 1H, J=8.4 Hz), 7.84 (d, 1H, J=8 Hz), 7.74 (m, 1H), 7.58 (m, 1H), 6.91 (d, 1H, J=8 Hz). MS m/z 202 (m+1).

Preparation of (4-Thiocyanato-naphthalen-1-yloxy)-acetic acid methyl ester (3B)

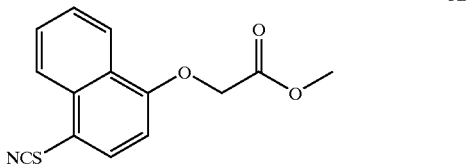

3B

The title compound was prepared in the manner analogous to example 1B utilizing compound 3A. 400 MHz $^1$H NMR (DMSO-$d_6$) δ 8.31 (d, 1H, J=8.4 Hz), 8.22 (d, 1H, J=8.4 Hz), 7.95 (d, 1H, J=8 Hz), 7.81 (m, 1H), 7.69 (m, 1H), 7.01 (d, 1H, J=8 Hz), 5.08 (s, 2H), 3.69 (s, 3H). MS m/z 274 (m+1).

Preparation of (4-Mercapto-naphthalen-1-yloxy)-acetic acid methyl ester (compound 3C)

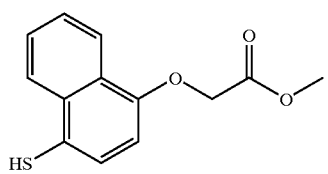

3C

The title compound was prepared in the manner analogous to example 1D utilizing compound 3B. 400 MHz $^1$H NMR (DMSO-$d_6$) δ 8.20 (d, 1H, J=8.4 Hz), 8.05 (d, 1H, J=8.4 Hz), 7.60 (m, 1H), 7.56 (m, 1H), 7.50 (d, 1H, J=8 Hz), 6.8 (d, 1H, J=8 Hz), 5.32 (s, 1H), 4.94 (s, 2H), 3.67 (s, 3H). MS m/z 249 (m+1).

Preparation of {4-[4-Methyl-2-(4-trifluoromethyl-phenyl)-thiazol-5-ylmethylsulfanyl]-naphthalen-1-yloxy}-acetic acid methyl ester (compound 3D)

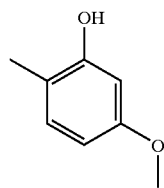

3D

The title compound was prepared in the manner analogous to example 1E utilizing compound 3C. 400 MHz $^1$H NMR (DMSO-$d_6$) δ 8.29 (d, 1H, J=8.4 Hz), 8.21 (d, 1H, J=8 Hz), 7.93 (d, 2H, J=8 Hz), 7.74 (d, 2H, J=8.4 Hz), 7.55 (m, 2H), 7.49 (d, 1H, J=8 Hz), 6.81 (d, 1H, J=8 Hz), 4.97 (s, 2H), 4.23 (s, 2H), 3.65 (s, 3H), 1.86 (s, 3H). MS m/z 504 (M+1).

Preparation of {4-[4-Methyl-2-(4-trifluoromethyl-phenyl)-thiazol-5-ylmethylsulfanyl]-naphthalen-1-yloxy}-acetic acid (Compound 3)

The title compound was prepared in the manner analogous to example 1 utilizing compound 3D. mp 181–183° C.; IR (thin film) cm$^{-1}$: 2924, 1719, 1323, 1110; 400 MHz $^1$H NMR (DMSO-$d_6$) δ 13.1 (br, 1H), 8.28 (d, 2H, J=7.2 Hz), 8.22 (d, 2H, J=7.2 Hz), 7.94 (d, 2H, J=8 Hz), 7.75 (d, 2H, J=8 Hz), 7.54 (m, 2H), 7.52 (d, 1H, J=8 Hz), 6.80 (d, 1H, J=8 Hz), 4.85 (s, 2H), 4.29 (s, 2H) 1.87 (s, 3H). MS m/z 490 (M+1). Anal. Calc'd for $C_{24}H_{18}F_3NO_3S_2$ C, 58.88; H, 3.71; N, 2.86; found: C, 58.40; H, 3.62; N, 2.76.

EXAMPLE 4

Synthesis of 2-[6-methyl-8-({4-methyl-2-[4-(trifluoromethyl)phenyl](1,3-thiazol-5-yl)}methylthio)chroman-5-yloxy]acetic acid (Compound 4)

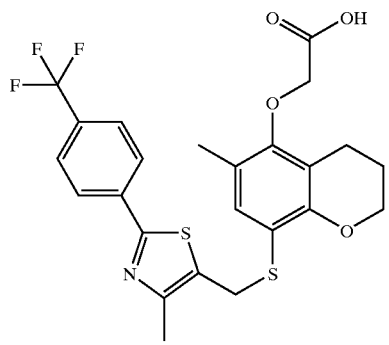

4

Preparation of 5-methoxy-2-methylphenol (Compound 4A)

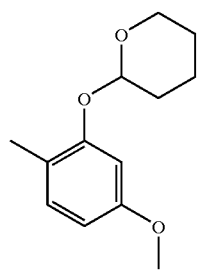

4A

A mixture of 2-hydroxy-4-methoxy-benzaldehyde (30.4 g, 0.20 mol), palladium/carbon (10%, 50% water, 30 g), concentrated HCl (15 ml) in 1500 ml of ethyl acetate was hydrogenated at 50 psi, at room temperature overnight, then filtered through Celite®. The filtrate was washed with water, brine, dried over sodium sulfate, concentrated, and purified using normal phase chromatography. 400 MHz $^1$H NMR (CDCl$_3$) δ 7.01 (d, 1H), 6.44–6.38 (m, 2H), 4.65 (s, 1H), 3.79 (s, 3H), 2.18 (s, 3H).

Preparation of 4-methoxy-1-methyl-2-perhydropyran-2-yloxybenzene (Compound 4B)

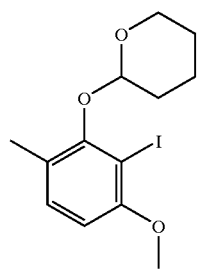

4B

To a solution of the product from example 4A (18.6 g, 0.135 mol) in dichloromethane (250 ml) was added 3,4-dihydro-2H-pyran (28.4 g, 0.338 mol) and pyridinium p-toluenesulfonate (1.70 g, 6.75 mmol) at room temperature. This solution was stirred at room temperature overnight, then quenched with saturated sodium bicarbonate (40 ml). The organics were separated, and the aqueous was extracted twice with dichloromethane (100 ml). The combined organics were washed with brine, dried over sodium sulfate, and concentrated to give 4B in good purity. 400 MHz $^1$H NMR (CDCl$_3$) δ 7.04 (d, 1H), 6.72 (d, 1H), 6.44 (dd, 1H), 5.40 (t, 1H), 3.92 (m, 1H), 3.76 (s, 3H), 3.61 (m, 1H), 2.19 (s, 3H), 2.02 (m, 1H), 1.88 (m, 2H), 1.65 (m, 3H).

Step 3. Preparation of 3-iodo-4-methoxy-1-methyl-2-perhydropyran-2-yloxybenzene (Compound 4C)

4C

To a solution of the product from example 4B (27.1 g, 0.122 mol) in heptane (500 ml) was added butyllithium (2.5 M solution in hexanes, 73.2 ml, 0.183 mol) at 0° C. The solution was stirred at 0° C. for 3 h, then a solution of iodine (52.6 g) in 600 ml of diethyl ether was added slowly at 0° C. The reaction mixture was stirred at 0° C. for 30 minutes, then quenched with saturated sodium thiosulfate (800 ml), and extracted with diethyl ether (3×800 ml). The combined organics were washed with sodium thiosulfate, brine, dried over sodium sulfate, and concentrated to give 4C in good purity. 400 MHz $^1$H NMR (CDCl$_3$) δ 7.10 (d, 1H), 6.58 (d, 1H), 5.08 (m, 1H), 4.17 (m, 1H), 3.89 (s, 3H), 3.52 (m, 1H), 2.38 (s, 3H), 2.16–1.24 (m, 6H).

Preparation of 2-iodo-4-methyl-3-perhydropyran-2-yloxyphenol (Compound 4D)

Sodium ethanethiolate (80%, 12.62 g, 0.12 mol) was added to a solution of the product from example 4C (20.88 g, 0.06 mol) in 200 ml of 1-methyl-2-pyrrolidinone at room temperature, then the mixture was heated at 160° C. for 20 minutes. After cooling, 2 N HCl was added to pH 6~7, and extracted with ethyl acetate. The organics were washed with brine, dried over sodium sulfate, concentrated, and purified using normal phase chromatography to afford the title product. 400 MHz $^1$H NMR (CDCl$_3$) δ 7.02 (d, 1H), 6.76 (d, 1H), 5.30 (s, 1H), 5.03 (m, 1H), 4.16 (m, 1H), 3.55 (m, 1H), 2.35 (s, 3H), 2.04–1.62 (m, 6H).

Preparation of 4-(3-bromopropoxy)-3-iodo-1-methyl-2-perhydropyran-2-yloxybenzene (Compound 4E)

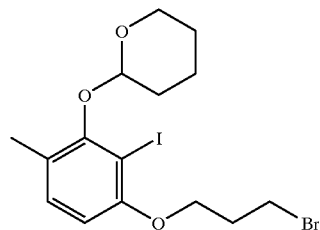

4E

To the product from example 4D (20.04 g, 0.06 mol) in 200 ml of DMF was added sodium hydride (60% in mineral oil, 4.8 g, 0.12 mol) portionwise at 0° C., then stirred at room temperature for 30 minutes. 1,3-Dibromopropane (14.54 g, 0.072 mol) was added and the mixture was stirred at room temperature for 30 minutes, then poured onto ice, extracted with diethyl ether, washed with brine, dried over sodium sulfate, concentrated, and purified using normal phase chromatography to afford the title product. 400 MHz $^1$H NMR (CDCl$_3$) δ 7.06 (d, 1H), 6.58 (d, 1H), 5.09 (m, 1H), 4.14 (m, 3H), 3.74 (t, 2H), 3.55 (m, 1H), 2.39 (m, 2H), 2.37 (s, 3H), 2.16–1.62 (m, 6H).

Preparation of 6-methyl-5-perhydropyran-2-yloxychromane (Compound 4F)

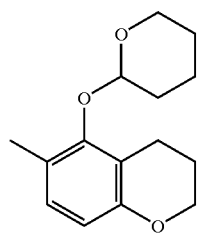

4F

To the product from example 4E (13.65 g, 0.030 mol) in 250 ml of THF was added butyllithium (2.5 M solution in hexanes, 13.2 ml, 0.033 mol) dropwise at −78° C., and stirred at the same temperature for 30 minutes, then quenched with saturated ammonium chloride solution, warmed to room temperature, extracted with diethyl ether, washed with brine, dried over sodium sulfate, concentrated, and purified using normal phase chromatography to afford the title product. 400 MHz $^1$H NMR (CDCl$_3$) δ 6.89 (d, 1H), 6.56 (d, 1H), 4.83 (m, 1H), 4.10 (m, 3H), 3.55 (m, 1H), 2.92 (m, 1H), 2.76 (m, 1H), 2.22 (s, 3H), 1.96–1.60 (m, 8H).

Preparation of 6-methylchroman-5-ol (Compound 4G)

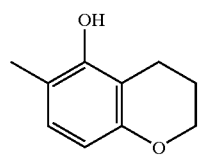

4G

The mixture of the product from example 4F (94.96 g, 0.02 mol) and pyridinium p-toluenesulfonate (600 mg) in ethanol (200 ml) was heated at 70° C. for 2 h, then cooled to room temperature, and the solvent was removed in vacuo. The residue was dissolved in ethyl acetate, washed with brine, dried over sodium sulfate, and concentrated to give 4G in good purity. 400 MHz $^1$H NMR (CDCl$_3$) δ 6.84 (d, 1H), 6.40 (d, 1H), 4.60 (s, 1H), 4.12 (m, 2H), 2.64 (m, 2H), 2.18 (s, 3H), 2.02 (m, 2H).

Preparation of methyl 2-(6-methylchroman-5-yloxy)acetate (Compound 4H)

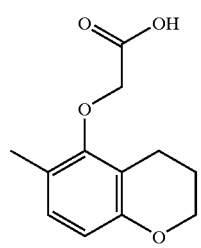

4H

The mixture of the product from example 4G (3.28 g, 0.020 mol), methyl bromoacetate (3.36 g, 0.022 mol), and cesium carbonate (9.77 g, 0.030 mol) in 100 ml of anhydrous acetonitrile was heated at 60° C. for 2 h. After cooling, the reaction mixture was filtered through Celite®. The filtrate was diluted with 500 ml of diethyl ether, washed with brine, dried over sodium sulfate, and concentrated to give 4H in good purity. 400 MHz $^1$H NMR (CDCl$_3$) δ 6.90 (d, 1H), 6.58 (d, 1H), 4.41 (s, 2H), 4.12 (m, 2H), 3.83 (s, 3H), 2.79 (t, 2H), 2.21 (s, 3H), 1.98 (m, 2H).

Preparation of methyl 2-(8-cyanothio-6-methylchroman-5-yloxy)acetate (Compound 4I)

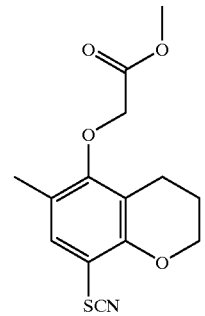

4I

To a stirred solution of the product from example 4H (4.72 g, 0.02 mol), sodium thiocyanate (6.48 g, 0.08 mol), and sodium bromide (2.06 g, 0.02 mol) in 15 ml of methanol at 0° C. was added a solution of bromine (3.52 g, 0.022 mol) in 15 ml of methanol dropwise over 20 minutes. After the completion of the bromine addition, the reaction mixture was stirred at room temperature for 1 h, then concentrated in vacuo to about 5 ml. The resulting residue was taken up in ethyl acetate (500 ml), washed with saturated sodium bicarbonate solution, brine, dried over sodium sulfate, concentrated, and purified using normal phase chromatography to afford the title product. 400 MHz $^1$H NMR (CDCl$_3$) δ 7.20 (s, 1H), 4.42 (s, 2H), 4.26 (m, 2H), 3.83 (s, 3H), 2.80 (t, 2H), 2.24 (s, 3H), 2.00 (m, 2H).

Preparation of methyl 2-(6-methyl-8-sulfanylchroman-5-yloxy)acetate (Compound 4J)

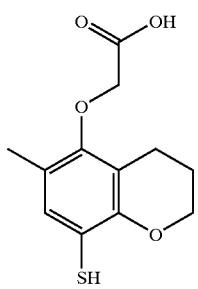

4J

A solution of the product from example 4I (5.16 g, 17.6 mmol), dithiothreitol (5.43 g, 35.2 mmol), and 0.2 M potassium dihydrogenphosphate (25 ml) in 100 ml of methanol was refluxed for 1 h under nitrogen, then cooled and concentrated in vacuo. The resulting residue was taken up in diethyl ether (200 ml), and washed with brine, dried over sodium sulfate, concentrated, and purified using normal phase chromatography to afford the title product. 400 MHz $^1$H NMR (CDCl$_3$) δ 6.93 (s, 1H), 4.41 (s, 2H), 4.22 (m, 2H), 3.82 s, 3H), 3.64 (s, 1H), 2.79 (t, 2H), 2.19 (s, 3H), 1.98 (m, 2H).

Preparation of methyl 2-[6-methyl-8-({4-methyl-2-[4-(trifluoromethyl)phenyl](1,3-thiazol-5-yl)}methylthio)chroman-5-yloxy]acetate (Compound 4K)

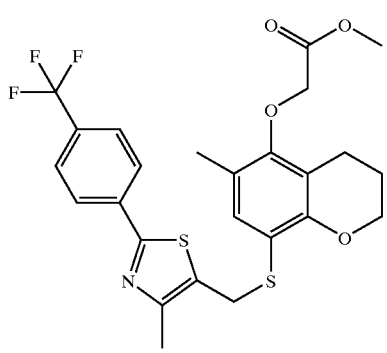

4K

The product from example 4J (0.80 g, 3.0 mmol) was dissolved in 20 ml anhydrous acetonitrile, then 5-(chloromethyl)-4-methyl-2-[4-(trifluoromethyl)phenyl]-1,3-thiazole (0.96 g, 3.3 mmol) was added followed by cesium carbonate (1.95 g, 6.0 mmol). The mixture was stirred at room temperature for 2 h, then filtered through Celite®, concentrated, and purified using normal phase chromatography to afford the title product. 400 MHz $^1$H NMR (CDCl$_3$) δ 7.98 (d, 2H), 7.64 (d, 2H), 6.98 (s, 1H), 4.40 (s, 2H), 4.25 (m, 2H), 4.18 (s, 2H), 3.82 (s, 3H), 2.80 (t, 2H), 2.28 (s, 3H), 2.15 (s, 3H), 1.97 (m, 2H).

Step 12. Preparation of 2-[6-methyl-8-({4-methyl-2-[4-(trifluoromethyl)phenyl](1,3-thiazol-5-yl)}methylthio)chroman-5-yloxy]acetic acid (Compound 4)

The product from example 41K (1.58 g, 2.98 mmol) was dissolved in a mixture of 20 ml of THF and 4 ml of water, then treated with lithium hydroxide monohydrate (0.38 g, 9.0 mmol). After stirring at room temperature for 1 h, the reaction mixture was acidified to pH 3 with 1 N HCl, then extracted with ethyl acetate (2×40 ml). The combined organics were washed with brine, dried over sodium sulfate, and concentrated. The title product was recrystallized from ethyl acetate/hexanes, mp 203.5–205.5° C.; 400 MHz $^1$H NMR (DMSO-d$_6$) δ 12.96 (brs, 1H), 8.06 (d, 2H), 7.82 (d, 2H), 6.98 (s, 1H), 4.38 (s, 2H), 4.35 (s, 2H), 4.17 (m, 2H), 2.71 (t, 2H), 2.30 (s, 3H), 2.10 (s, 3H), 1.84 (m, 2H). MS m/z 510 (M+1). Anal. Calc'd for C$_{24}$H$_{22}$NO$_4$S$_2$F$_3$: C, 56.57; H, 4.35; N, 2.75; Found: C, 56.18; H, 4.31; N, 2.68.

EXAMPLE 5

Synthesis of 2-[5-methyl-7-({4-methyl-2-[4-(trifluoromethyl)phenyl](1,3-thiazol-5-yl)}methylthio)-2,3-dihydrobenzo[b]furan-4-yloxy]acetic acid (Compound 5)

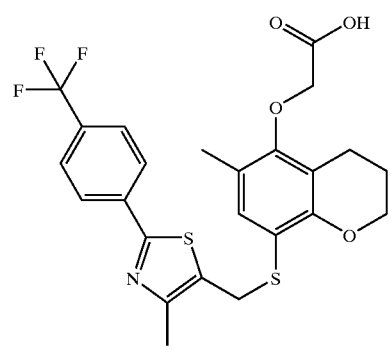

5

Preparation of 4-(2-bromoethoxy)-3-iodo-1-methyl-2-perhydropyran-2-yloxybenzene (compound 5A)

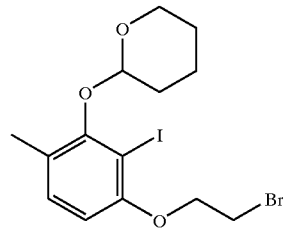

5A

A mixture of 4D (8.0 g, 0.023 mol), 1,2-dibromoethane (14.54 g, 0.072 mol), and cesium carbonate (23.25 g, 0.069 mol) in 30 ml of N,N-dimethylformamide was heated at 80° C. for 2 h, then cooled, and filtered through Celite®. To the filtrate, 500 ml of ethyl acetate was added, washed with water, brine, dried over anhydrous sodium sulfate, and concentrated to give 5A in good purity. 400 MHz $^1$H NMR (CDCl$_3$) δ 7.08 (d, 1H), 6.54 (d, 1H), 5.07 (m, 1H), 4.30 (t, 2H), 4.12 (m, 1H), 3.69 (t, 2H), 3.50 (m, 1H), 2.30 (s, 3H), 2.17–1.52 (m, 6H).

Preparation of 5-methyl-4-perhydropyran-2-yloxy-2,3-dihydrobenzo[b]furan (Compound 5B)

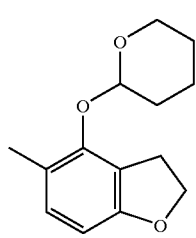

5B

To the product from example 5A (7.27 g, 0.0164 mol) in 100 ml of tetrahydrofuran and 30 ml of hexane, n-buthyllithium (2.5 M in hexane, 7.9 ml, 0.0196 mol) was added dropwise over 30 minutes at −78° C., and allowed to stir at the same temperature for 1 h and at ambient temperature for 1.5 h, extracted with ethyl acetate (3×100 ml), washed with water, brine, dried over anhydrous sodium sulfate, concentrated and used for the next step without further purification. 400 MHz $^1$H NMR (CDCl$_3$) δ 6.90 (d, 1H), 6.45 (d, 1H), 5.10 (m, 1H), 4.55 (t, 2H), 4.01 (m, 1H), 3.60 (m, 1H), 3.30 (t, 2H), 2.20 (s, 3H), 1.90–1.80 (m, 3H), 1.70–1.55 (m, 3H).

Preparation of 5-methyl-2,3-dihydrobenzo[b]furan-4-ol (Compound 5C)

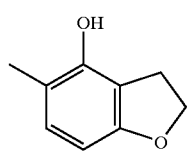

5C

A mixture of the product from example 5B (3.5 g, 0.014 mol), and pyridinium-p-toluenesulfonate (0.7 g) in methanol (50 ml) was refluxed for 2 h, then cooled and concentrated. The residue was dissolved in ethyl acetate (100 ml), washed with water, brine, dried over anhydrous sodium sulfate, concentrated, and purified using normal phase chromatography. 400 MHz $^1$H NMR (CDCl$_3$) δ 6.87 (d, 1H), 6.34 (d, 1H), 4.61 (t, 2H), 4.55 (s, 1H), 3.15 (t, 2H), 2.20 (s, 3H).

Preparation of (4-hydroxy-5-methyl-(2,3-dihydrobenzo[2,3-b]furan-7-yl))thiocarbonitrile (Compound 5D)

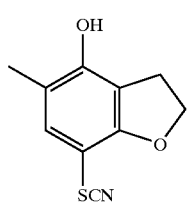

5D

The title compound was prepared in the manner analogous to Example 2A with the product from example 5C (1.47 g, 0.0098 mol), sodium thiocyanate (2.6 g, 0.03 mol), sodium bromide (0.99 g, 0.0098 mol), and bromine (1.67 g, 0.0107 mol) in 20 ml of anhydrous methanol. 400 MHz $^1$H NMR (CDCl$_3$) δ 7.08 (s, 1H), 4.85 (s, 1H), 4.73 (t, 2H), 3.22 (t, 2H), 2.20 (s, 3H).

Preparation of methyl 2-(7-cyanothio-5-methyl-2,3-dihydrobenzo[b]furan-4-yloxy)acetate (Compound 5E)

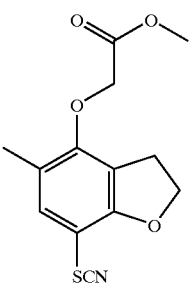

5E

The title compound was prepared in the manner analogous to Example 1B with the product from example 5D (1.98 g, 0.0095 mol), methylbromoacetate (1.60 g, 0.010 mol), and cesium carbonate (4.6 g, 0.014 mol) in 50 ml anhydrous acetonitrile. 400 MHz $^1$H NMR (CDCl$_3$) δ 7.12 (s, 1H), 4.70 (t, 2H), 4.62 (s, 2H), 3.81 (s, 3H), 3.35 (t, 2H), 2.22 (s, 3H).

Preparation of methyl 2-(5-methyl-7-sulfanyl-2,3-dihydrobenzo[b]furan-4-yloxy)acetate (Compound 5F)

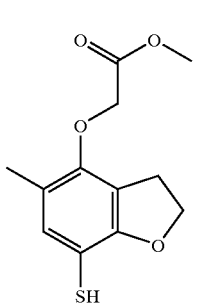

5F

The title compound was prepared in the manner analogous to Example 1D with the product from example 5E (2.6 g; 0.0093 mol), dithiothreitol (1.85 g; 0.0119 mol) and 0.2 M potassium dihydrogenphosphate (4.42 ml) in 40 ml of methanol. 400 MHz $^1$H NMR (CDCl$_3$) δ 6.87 (s, 1H), 4.69 (s, 2H), 4.52 (t, 2H), 3.70 (s, 3H), 3.27 (t, 2H), 2.10 (s, 3H).

Preparation of methyl 2-[5-methyl-7-({4-methyl-2-[4-(trifluoromethyl)phenyl](1,3-thiazol-5-yl)}methylthio)-2,3-dihydrobenzo[b]furan-4-yloxy]acetate (Compound 5G)

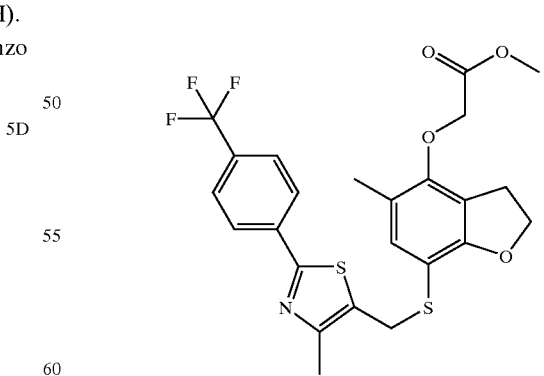

5G

The title compound was prepared in the manner analogous to Example 1E with the product from example 5F (600 mg, 2.36 mmol), 5-(chloromethyl)-4-methyl-2-[4-(trifluoromethyl)phenyl]-1,3-thiazole (760 mg, 2.59 mmol), and cesium carbonate (1.54 g, 4.72 mmol) in 25 ml of anhydrous acetonitrile. 400 MHz $^1$H NMR (CDCl$_3$) δ 7.97

(d, 2H), 7.64 (d, 2H), 6.90 (s, 1H), 4.60 (t, 2H), 4.55 (s, 2H), 4.17 (s, 2H), 3.80 (s, 3H), 3.29 (t, 2H), 2.25 (s, 3H), 2.14 (s, 3H).

Preparation of 2-[5-methyl-7-({4-methyl-2-[4-(trifluoromethyl)phenyl](1,3-thiazol-5-yl)}methylthio)-2,3-dihydrobenzo[b]furan-4-yloxy]acetic acid (Compound 5)

The title compound was prepared in the manner analogous to Example 1 with the product from example 5G (1.0 g, 0.0019 mol), and lithium hydroxide monohydrate (0.25 g, 0.0058 mol) in 15 ml of tetrahydrofuran/water mixture (10:1). mp 157–158° C. MS m/z 496 (M+1).

400 MHz $^1$H NMR (DMSO-d$_6$) δ 8.05 (d, 2H), 7.82 (d, 2H), 6.90 (s, 1H), 4.65 (s, 2H), 4.52 (t, 2H), 4.30 (s, 2H), 3.30 (t, 2H), 2.24 (s, 3H), 2.08 (s, 3H). Anal. Calc'd for C$_{23}$H$_{20}$NO$_4$S$_2$F$_3$: C, 55.75; H, 4.07; N, 2.83; found: C, 55.38; H, 4.18; N, 2.66.

EXAMPLE 6

Synthesis of {5-Methyl-7-[4-methyl-2-(4-trifluoromethyl-phenyl)-thiazol-5-ylmethylsulfanyl]-indan-4-yloxy}-acetic acid (Compound 6)

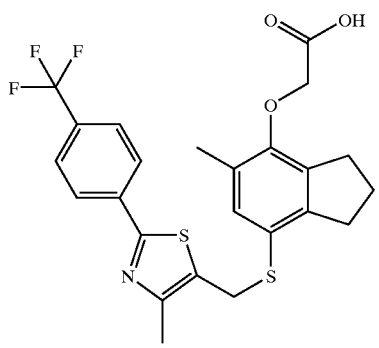

6

Preparation of {5-Methyl-7-[4-methyl-2-(4-trifluoromethyl-phenyl)-thiazol-5-ylmethylsulfanyl]-indan-4-yloxy}-acetic acid methyl ester (Compound 6A)

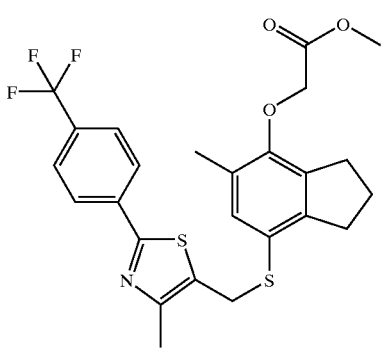

6A

The title compound was prepared from 5-(chloromethyl)-4-methyl-2-[4-(trifluoromethyl)phenyl]-1,3-thiazole and (7-mercapto-5-methyl-indan-4-yloxy)-acetic acid methyl ester (prepared in a similar manner as described for Example 1D) in a manner analogous to Example 1E. MS m/z 508 (M+1).

Preparation of {5-Methyl-7-[4-methyl-2-(4-trifluoromethyl-phenyl)-thiazol-5-ylmethylsulfanyl]-indan-4-yloxy}-acetic acid (Compound 6)

The title compound was prepared from the product of Example 6A in the manner analogous to Example 1. mp 184° C.; 400 MHz $^1$H NMR (DMSO-d$_6$) δ 12.83 (s, 1H), 7.82 (d, 2H, J=8 Hz), 7.76 (d, J=8.4 Hz), 7.00 (s, 1H), 4.43 (s, 2H), 4.29 (s, 2H), 2.83 (t, 2H, J=7.2 Hz), 2.65 (t, 2H, J=7.2 Hz), 2.16 (s, 3H), 2.12 (s, 3H), 1.86 (m, 2H). MS m/z 494 (M+1).

EXAMPLE 7

Synthesis of {7-[4-Methyl-2-(4-trifluoromethyl-phenyl)-thiazol-5-ylmethylsulfanyl]-indan-4-yloxy}-acetic acid (Compound 7)

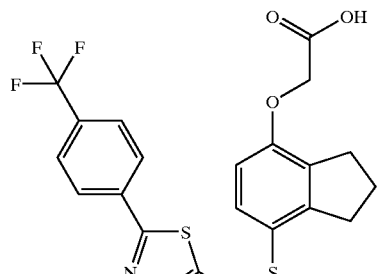

Preparation of Indan-4-ol (compound 7A)

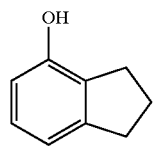

7A

A mixture of 4-hydroxy-indan-1-one (5.0 g, 33.7 mmol), sodium cyanoborohydride (6.4 g, 101.1 mmol), and zinc iodide (32.3 g, 101.1 mmol) in dichloroethane, was heated at reflux for two hours. The reaction mixture was then filtered through 50 g SiO$_2$ while still warm, eluting further with dichloroethane. The filtrate was collected and concentrated under vacuum. The residue was added to diethyl ether and the resulting white precipitate was filtered off. The filtrate was collected and concentrated in vacuo to give 4.2 g of the title compound with purity high enough for subsequent use. 400 MHz $^1$H NMR (DMSO-d$_6$) δ 9.06 (s, 1H), 6.86 (t, 1H, J=7.8 Hz), 6.59 (d, 1H, J=7.8 Hz), 6.48 (d, 1H, J=7.8 Hz), 2.75 (t, 2H, J=7.3 Hz), 2.67 (t, 2H, J=7.3 Hz), 1.92 (m, 2H).

Preparation of 7-Thiocyanato-indan-4-ol (compound 7B)

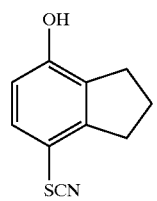

7B

The title compound was prepared in the manner analogous to Example 2A using the product from Example 7A. MS m/z 192 (M+1).

Preparation of (7-Mercapto-indan-4-yloxy)-acetic acid methyl ester (compound 7C)

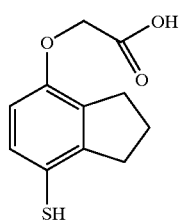

7-Thiocyanato-indan-4-ol (Example 7B) (1.47 g, 7.7 mmol), cesium carbonate (3.77 g, 11.6 mmol) and methyl bromoacetate (1.24 g, 8.08 mmol) were stirred in 20 ml acetonitrile at ambient temperature for 4 h. The reaction was filtered and concentrated. The crude product was treated under the conditions of Example 2D to afford the title product. MS m/z 239 (M+1).

Preparation of {7-[4-Methyl-2-(4-trifluoromethyl-phenyl)-thiazol-5-ylmethylsulfanyl]-indan-4-yloxy}-acetic acid methyl ester (Compound 7D)

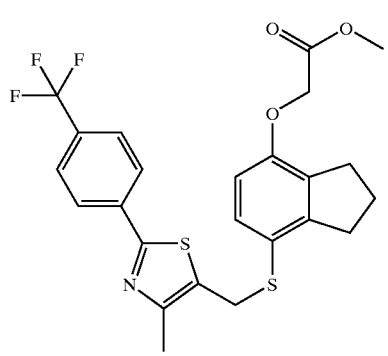

The title compound was prepared in the manner analogous to Example 1E using the products from Example 7C and 5-(chloromethyl)-4-methyl-2-[4-(trifluoromethyl)phenyl]-1,3-thiazole. MS m/z 494 (M+1).

Preparation of {7-[4-Methyl-2-(4-trifluoromethyl-phenyl)-thiazol-5-ylmethylsulfanyl]-indan-4-yloxy}-acetic acid (Compound 7)

The title compound was prepared in the manner analogous to Example 1 using the product from Example 7D. 400 MHz $^1$H NMR (DMSO-$d_6$) δ 7.99 (d, 2H, J=8.1 Hz), 7.77 (d, 2H, J=8.3 Hz), 7.09 (d, 1H, J=8.3 Hz), 6.59 (d, 1H, J=8.5 Hz), 4.63 (s, 2H), 4.22 (s, 2H), 2.75 (m, 4H), 2.09 (s, 3H), 1.89 (m, 2H). MS m/z 480 (M+1).

Biological Assays

The compounds of the present invention have demonstrated PPAR modulating activity in the standard assays commonly employed by those skilled in the art. Accordingly, such compounds and formulations comprising such compounds are useful for treating, preventing or controlling hypercholesterolemia and hyperlipidemia.

A. Selectivity Measurements

1. Test A. Transient Transfections Assay using the HepG2 Hepatoma Cell Line.

HepG2 cells were transiently transfected with an expression plasmids encoding hPPARα, hPPARβ or mPPARγ chimeric receptors and a reporter containing the yeast upstream activating sequence (UAS) upstream of the viral E1B promoter controlling a luciferase reporter gene. In addition, the plasmid pRSVβ-gal was used to control for transfection efficiency. HepG2 cells were grown in DMEM supplemented with 10% FBS and 1 μM non-essential amino acid. On the first day, cells were split into 100 mm dishes at 2.5×10$^6$/dish and incubated overnight at 37° C./5% CO$_2$. On the second day the cells were transiently transfected with plasmid DNA encoding a chimeric receptor, the luciferase reporter gene; and β-gal. For each 100 mm dish, 15 μg of lucifease reporter (PG5E1b) DNA, 15 μg of Gal4-PPAR chimeric receptor DNA, and 1.5 μg of β-gal plasmid DNA were mixed with 1.4 ml of opti-MEM in the tube. 28 μl of LipoFectamine-2000 reagent was added to 1.4 ml of opti-MEM in the tube, and incubate for 5 min at RT. The diluted Lipofectamine-2000 reagent was combined with the DNA mixture, and incubate for 20 min at RT. After fresh medium was added to each 100 mm dish of cells, 2.8 ml of Lipofectamine2000-DNA mixture was added dropwise to the 100 mm dish containing 14 ml of medium, and incubate 37° C. overnight. On day three cells were trypsinized off the 100 mm dishes and re-plated on 96 well plates. Cells were plated at 2.5×10$^4$ cells per well in 150 μl of media and 50 μl of compound diluted by media was added. The test compound added were in the range from 50 μM to 50 pM. After addition of compounds, the plates were incubated at 37° C. for 24 hours. Subsequently cells were washed with once with 100 μl of PBS, lysed, and processed for measuring luciferase and β-gal activity using Dual-Light luciferase kit from Tropix®, according to the manufacturer's recommendations, on an EG&G Bethold MicroLumat LB96P luminometer. EC$_{50}$ values were obtained using the GraphPad Prism™ program. Surprisingly, the compounds of the present invention exhibit activity for both PPARα and PPARβ. Accordingly, the compounds of the present invention should find considerable therapeutic applications for hypercholesterolemia and hyperlipidemia. The Hep G2-hBeta EC$_{50}$ ("EC$_{50}$β") data as well as the Hep G2-hAlpha EC$_{50}$ ("EC$_{50}$α") data of the compounds of the invention are shown in Table 1 below.

TABLE 1

| Example | Hep G2-hβ EC$_{50}$ nM | Hep G2-hα EC$_{50}$ nM |
| --- | --- | --- |
| 1 | 187 | 402694 |
| 2 | 52 | 2966 |
| 3 | 76 | 3581 |
| 4 | 45 | 1761 |
| 5 | 0.8 | 52 |
| 6 | 133 | 191 |
| 6 | 34 | 2716 |

Formulations

The compounds of the present invention can be administered alone or in combination with one or more therapeutic agents. These include, for example, other agents for treating, preventing or controlling dyslipidemia, non-insulin dependent diabetes mellitus, obesity, hyperglycemia, hypercholesteremia, hyperlipidemia, atherosclerosis, hypertriglyceridemia, or hyperinsulinemia.

The compounds are thus well suited to formulation for convenient administration to mammals for the prevention and treatment of such disorders.

The following examples further illustrate typical formulations provided by the invention.

41

| Formulation 1 | |
|---|---|
| Ingredient | Amount |
| compound of Formulae I-III | 0.5 to 800 mg |
| sodium benzoate | 5 mg |
| isotonic saline | 1000 mL |

The above ingredients are mixed and dissolved in the saline for IV administration to a patient.

| Formulation 2 | |
|---|---|
| Ingredient | Amount |
| compound of Formulae I-III | 0.5 to 800 mg |
| cellulose, microcrystalline | 400 mg |
| stearic acid | 5 mg |
| silicon dioxide | 10 mg |
| sugar, confectionery | 50 mg |

The ingredients are blended to uniformity and pressed into a tablet that is well suited for oral administration to a patient.

| Formulation 3 | |
|---|---|
| Ingredient | Amount |
| compound of Formulae I-III | 0.5 to 800 mg |
| starch, dried | 250 mg |
| magnesium stearate | 10 mg |

The ingredients are combined and milled to afford material suitable for filling hard gelatin capsules administered to patient.

| Formulation 4 | |
|---|---|
| Ingredient | Amount % wt./(total wt.) |
| compound of Formulae I-III | 1 to 50 |
| Polyethylene glycol 1000 | 32 to 75 |
| Polyethylene glycol 4000 | 16 to 25 |

The ingredients are combined via melting and then poured into molds containing 2.5 g total weight.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

42

What is claimed is:

1. A compound having formula I:

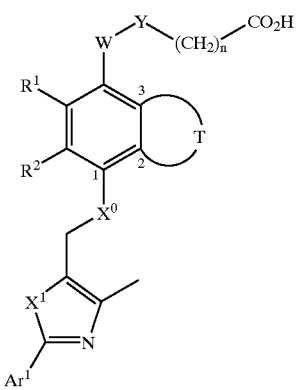

or a pharmaceutically acceptable salt thereof, wherein:

T is a saturated or unsaturated, substituted or unsubstituted hydrocarbon chain or hydrocarbon-heteroatom chain having from 3 to 6 atoms wherein the carbon atom of position 2 is connected to the carbon atom of position 3 to form a five to eight member ring;

W is O, S, $CH_2$, $CR^4R^5$, $NR^3$, cycloalkylene, or heterocycloalkylene;

Y is absent, O, or $CR^4R^5$ wherein
Y is $CR^4R^5$ or absent when W is O, S, or $NR^3$; and
Y is O or absent when W is $CH_2$ or $CR^4R^5$;

$R^1$ and $R^2$ are independently hydrogen, lower alkyl, lower alkoxy, haloalkyl, —O—$(CH_2)_pCF_3$, halogen, nitro, cyano, —OH, —SH, —$CF_3$, —$S(O)_p$alkyl, $S(O)_p$aryl, —$(CH_2)_mOR^3$, —$(CH_2)_mNR^6R^7$, —$COR^3$, —$CO_2H$, —$CO_2R^3$, or —$NR^6R^7$;

$R^3$ is hydrogen, alkyl, alkenyl, alkynyl, or aryl;

$R^4$ and $R^5$ are independently hydrogen, alkyl, alkenyl, alkynyl, or aryl, or joined together to form a 4 to 7 member ring having 0 to 3 heteroatoms;

$R^6$ and $R^7$ are independently hydrogen, alkyl, alkenyl, alkynyl, —COalkyl, —COaryl, cycloalkyl, —$CO_2$alkyl, —$CO_2$aryl, —$SO_2$alkyl, —$SO_2$aryl, or joined together to form a 4 to 7 member ring having 1 to 3 heteroatoms;

$X^0$ and $X^1$ are independently O or S;

$Ar^1$ is substituted or unsubstituted aryl or heteroaryl;

m is 0 to 5;

n is 0 to 5; and p is 0 to 2.

2. The compound of claim 1, wherein W is O, Y is absent, and n is 1.

3. The compound of claim 1, wherein T is substituted with 1 or more substituents selected from lower alkyl, lower alkoxy, lower thioalkoxy, —$O(CH_2)_{0-2}CF_3$, halogen, nitro, cyano, =O, =S, —OH, —SH, —$CF_3$, —$OCF_3$, —$CO_2H$, —$CO_2C_1$-$C_6$ alkyl, —$NH_2$, —$NHC_1$-$C_6$ alkyl, —$OCH_2O$—, and —$N(C_1$-$C_6$alkyl$)_2$.

4. The compound of claim 1, wherein:

T is —$CH_2CH_2CO$—O—, —$CH_2$—$CH_2$—O—CO—, —$CH_2$—$CH_2$—$CH_2$—$CH_2$—, —HC=CH—HC=CH—, —N=CH—HC=CH—, —HC=N—HC=CH—, —HC=CH—N=CH—, —HC=CH—HC=N—, —$CH_2$—$CH_2$—$CH_2$—, —$CH_2$—$CH_2$—

O—CH$_2$—, —CH$_2$—HC=CH—CH$_2$—, —CH$_2$—HC=CH—, —CH$_2$CH$_2$—NH—CH$_2$—, —COCH=CH—O—, —O—CH=CH—CO—, —CH=CH—NR$^4$—, —NR$^4$—CH=CH—, —CH=CH—CH$_2$—, —CH$_2$—CH$_2$—NR$^4$—, —NR$^4$—CH$_2$—CH$_2$—, —O—CH$_2$—CH$_2$—, —CH$_2$—CH$_2$—O—, —CH$_2$—CH$_2$CO—, —CH$_2$—CO—CH$_2$-, —CO—CH$_2$—CH$_2$—, —CH$_2$—CH$_2$—CH$_2$—CO—, —CO—CH$_2$—CH$_2$—CH$_2$—, —CH$_2$—CO—CH$_2$—CH$_2$—, —CH$_2$—CH$_2$—CO—CH$_2$—, —CH$_2$—CH$_2$—CH$_2$—NR$^4$—, —NR$^4$—CH$_2$—CH$_2$—CH$_2$—, —O—CH$_2$—CH$_2$—CH$_2$—, —CH$_2$—CH$_2$—CH$_2$—O—, —CO—NR$^4$—CH$_2$—CH$_2$—, NR$^4$CO—CH$_2$—CH$_2$—, —CH$_2$—CH$_2$_NR$^4$—CO—, or —CH$_2$—CH$_2$—CO—NR$^4$—.

5. The compound of claim 1, wherein:
R$^1$ and R$^2$ are independently hydrogen, alkyl, or alkoxy.

6. The compound of claim 1, wherein:
R$^1$ is hydrogen; and
R$^2$ is alkyl or alkoxy.

7. The compound of claim 1, wherein:
R$^1$ is hydrogen; and
R$^2$ is alkoxy.

8. The compound of claim 1, wherein:
R$^1$ is hydrogen, methyl, ethyl, isopropyl, n-propyl, t-butyl, n-butyl, or isobutyl; and
R$^2$ is methyoxy, ethoxy, isopropoxy, n-propoxy, t-butoxy, n-butoxy, or isobutoxy.

9. A compound having Formula IIa, Formula IIb, Formula IIc, Formula IId, or Formula IIe:

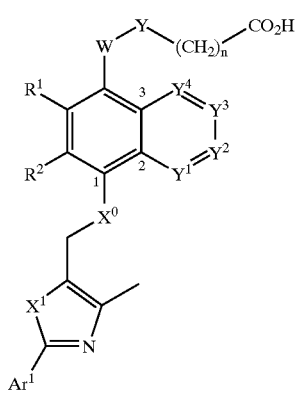

IIa

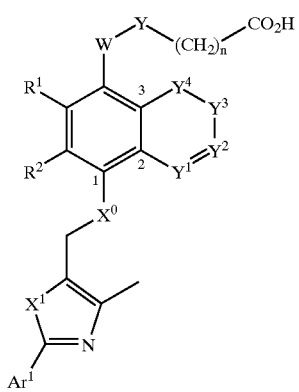

IIb

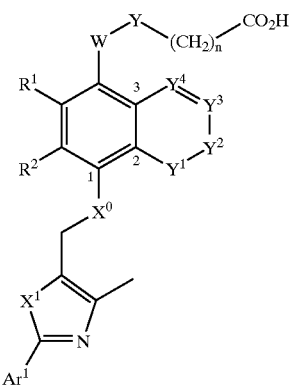

IIc

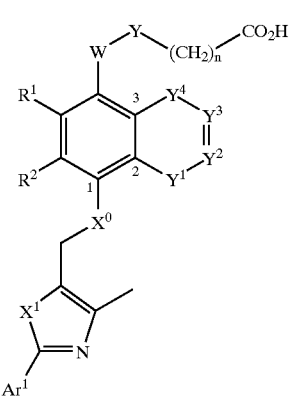

IId

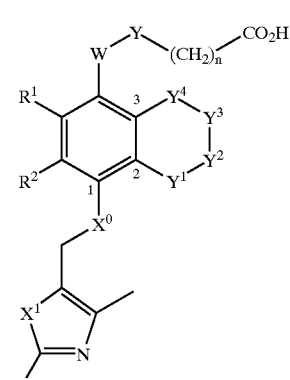

IIe or a pharmaceutically acceptable salt thereof,
wherein:
Y$^1$, Y$^2$, Y$^3$ and Y$^4$ are independently a carbon atom or a heteroatom wherein the carbon atom and the heteroatom are bonded to a sufficient number of hydrogen atoms or substituents to complete the valency of each atom with the proviso that Y$^1$, Y$^2$, Y$^3$ and Y$^4$ are not all heteroatoms and that not more than two adjacent atoms in Y$^1$, Y$^2$, Y$^3$ and Y$^4$ are heteroatoms and that in Formulae IIb, IIc, and IId, Y$^1$, Y$^2$, Y$^3$ and Y$^4$ are not all carbon;
W is O, S, CH$_2$, CR$^4$R$^5$, NR$^3$, cycloalkylene, or heterocycloalkylene;
Y is absent, O, or CR$^4$R$^5$ wherein
Y is CR$^4$R$^5$ or absent when W is O, S, or NR$^3$; and
Y is O or absent when W is CH$_2$ or CR$^4$R$^5$;

$R^1$ and $R^2$ are independently hydrogen, lower alkyl, lower alkoxy, haloalkyl, —O—$(CH_2)_pCF_3$, halogen, nitro, cyano, —OH, —SH, —$CF_3$, —$S(O)_p$alkyl, $S(O)_p$aryl, —$(CH_2)_mOR^3$, —$(CH_2)_mNR^6R^7$, —$COR^3$, —$CO_2H$, —$CO_2R^3$, or —$NR^6R^7$;

$R^3$ is hydrogen, alkyl, alkenyl, alkynyl, or aryl;

$R^4$ and $R^5$ are independently hydrogen, alkyl, alkenyl, alkynyl, or aryl, or joined together to form a 4 to 7 member ring having 0 to 3 heteroatoms;

$R^6$ and $R^7$ are independently hydrogen, alkyl, alkenyl, alkynyl, —COalkyl, —COaryl, cycloalkyl, —$CO_2$alkyl, —$CO_2$aryl, —$SO_2$alkyl, —$SO_2$aryl, or joined together to form a 4 to 7 member ring having 1 to 3 heteroatoms;

$X^0$ and $X^1$ are independently O or S;

$Ar^1$ is substituted or unsubstituted aryl or heteroaryl;

m is 0 to 5;

n is 0 to 5; and p is 0 to 2.

10. The compound of claim 9, wherein W is O, Y is absent, and n is 1.

11. The compound of claim 9, wherein the heteroatom is N, O, or S.

12. The compound of claim 9, wherein:

$R^1$ and $R^2$ are independently hydrogen, alkyl, or alkoxy.

13. The compound of claim 9, wherein:

$R^1$ is hydrogen; and $R^2$ is alkyl or alkoxy.

14. The compound of claim 9, wherein:

$R^1$ is hydrogen; and $R^2$ is alkoxy.

15. The compound of claim 9, wherein:

$R^1$ is hydrogen, methyl, ethyl, isopropyl, n-propyl, t-butyl, n-butyl, or isobutyl; and $R^2$ is methyoxy, ethoxy, isopropoxy, n-propoxy, t-butoxy, n-butoxy, or isobutoxy.

16. A compound having Formula IIIa, Formula IIIb, or Formula IIIc:

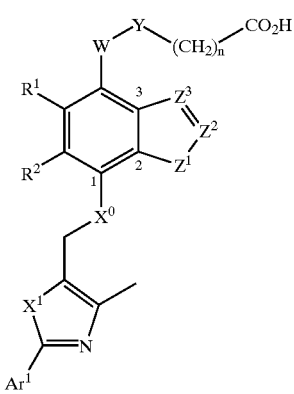

IIIa

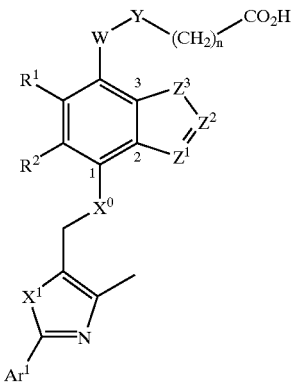

IIIb

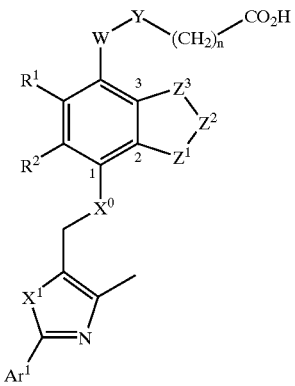

IIIc or a pharmaceutically acceptable salt thereof,
wherein:
W is O, S, $CH_2$, $CR^4R^5$, $NR^3$, cycloalkylene, or heterocycloalkylene;
Y is absent, O, or $CR^4R^5$ wherein
Y is $CR^4R^5$ or absent when W is O, S, or $NR^3$; and
Y is O or absent when W is $CH_2$ or $CR^4R^5$;
$R^1$ and $R^2$ are independently hydrogen, lower alkyl, lower alkoxy, haloalkyl, —O—$(CH_2)_pCF_3$, halogen, nitro, cyano, —OH, —SH, —$CF_3$, —$S(O)_p$alkyl, $S(O)_p$aryl, —$(CH_2)_mOR^3$, —$(CH_2)_mNR^6R^7$, —$COR^3$, —$CO_2H$, —$CO_2R^3$, or —$NR^6R^7$;
$R^3$ is hydrogen, alkyl, alkenyl, alkynyl, or aryl;
$R^4$ and $R^5$ are independently hydrogen, alkyl, alkenyl, alkynyl, or aryl, or joined together to form a 4 to 7 member ring having 0 to 3 heteroatoms;
$R^6$ and $R^7$ are independently hydrogen, alkyl, alkenyl, alkynyl, —COalkyl, —COaryl, cycloalkyl, —$CO_2$alkyl, —$CO_2$aryl, —$SO_2$alkyl, —$SO_2$aryl, or joined together to form a 4 to 7 member ring having 1 to 3 heteroatoms;
$X^0$ and $X^1$ are independently O or S;
$Ar^1$ is substituted or unsubstituted aryl or heteroaryl;
m is 0 to 5;
n is 0 to 5;
p is 0 to 2; and
$Z^1$, $Z^2$, and $Z^3$ are independently a carbon atom or a heteroatom wherein the carbon atom and the heteroatom are bonded to a sufficient number of hydrogen atoms or substituents to complete the valency of each atom with the proviso that $Z^1$, $Z^2$, and $Z^3$ are not all heteroatoms and that in Formulae IIIa and IIIb $Z^1$, $Z^2$, and $Z^3$ are not all carbon atoms.

17. The compound of claim 16, wherein W is O, Y is absent, and n is 1.

18. The compound of claim 16, wherein:
$R^1$ and $R^2$ are independently hydrogen, alkyl, or alkoxy.

19. The compound of claim 16, wherein:
$R^1$ is hydrogen; and
$R^2$ is alkyl or alkoxy.

20. The compound of claim 16, wherein:
$R^1$ is hydrogen; and
$R^2$ is alkoxy.

21. The compound of claim 16, wherein:
$R^1$ is hydrogen, methyl, ethyl, isopropyl, n-propyl, t-butyl, n-butyl, or isobutyl; and
$R^2$ is methyoxy, ethoxy, isopropoxy, n-propoxy, t-butoxy, n-butoxy, or isobutoxy.

22. A compound selected from
{4-[4-Methyl-2-(4-trifluoromethyl-phenyl)-thiazol-5-ylmethylsulfanyl]-5-oxo-5,6,7,8-tetrahydro-naphthalen-1-yloxy}-acetic acid;
{4-[4-Methyl-2-(4-trifluoromethyl-phenyl)-thiazol-5-ylmethylsulfanyl]-8-oxo-5,6,7,8-tetrahydro-naphthalen-1-yloxy}-acetic acid;
{4-[4-Methyl-2-(4-trifluoromethyl-phenyl)-thiazol-5-ylmethylsulfanyl]-7-oxo-5,6,7,8-tetrahydro-naphthalen-1-yloxy}-acetic acid;
{4-[4-Methyl-2-(4-trifluoromethyl-phenyl)-thiazol-5-ylmethylsulfanyl]-6-oxo-5,6,7,8-tetrahydro-naphthalen-1-yloxy}-acetic acid;
{5-[4-Methyl-2-(4-trifluoromethyl-phenyl)-thiazol-5-ylmethylsulfanyl]-4-oxo-4H-chromen-8-yloxy}-acetic acid;
{8-[4-Methyl-2-(4-trifluoromethyl-phenyl)-thiazol-5-ylmethylsulfanyl]-4-oxo-4H-chromen-5-yloxy}-acetic acid;
{8-[4-Methyl-2-(4-trifluoromethyl-phenyl)-thiazol-5-ylmethylsulfanyl]-4-oxo-chroman-5-yloxy}-acetic acid;
{5-[4-Methyl-2-(4-trifluoromethyl-phenyl)-thiazol-5-ylmethylsulfanyl]-4-oxo-chroman-8-yloxy}-acetic acid;
{8-[4-Methyl-2-(4-trifluoromethyl-phenyl)-thiazol-5-ylmethylsulfanyl]-quinolin-5-yloxy}-acetic acid;
{8-[4-Methyl-2-(4-trifluoromethyl-phenyl)-thiazol-5-ylmethylsulfanyl]-isoquinolin-5-yloxy}-acetic acid;
{1-Methyl-7-[4-methyl-2-(4-trifluoromethyl-phenyl)-thiazol-5-ylmethylsulfanyl]-1H-benzoimidazol-4-yloxy}-acetic acid;
{3-Methyl-7-[4-methyl-2-(4-trifluoromethyl-phenyl)-thiazol-5-ylmethylsulfanyl]-1H-benzoimidazol-4-yloxy}-acetic acid;
{7-[4-Methyl-2-(4-triluoromethyl-phenyl)-thiazol-5-ylmethylsulfanyl]-1H-indol-4-yloxy}-acetic acid;
{1-Methyl-7-[4-methyl-2-(4-trifluoromethyl-phenyl)-thiazol-5-ylmethylsulfanyl]-1H-indol-4-yloxy}-acetic acid;
{7-[4-Methyl-2-(4-trifluoromethyl-phenyl)-thiazol-5-ylmethylsulfanyl]-benzo[b]thiophen-4-yloxy}-acetic acid;
{7-[4-Methyl-2-(4-trifluoromethyl-phenyl)-thiazol-5-ylmethylsulfanyl]-benzofuran-4-yloxy}-acetic acid;
{8-[4-Methyl-2-(4-trifluoromethyl-phenyl)-thiazol-5-ylmethylsulfanyl]-chroman-5-yloxy}-acetic acid;
{4-[4-Methyl-2-(4-trifluoromethyl-phenyl)-thiazol-5-ylmethylsulfanyl]-5,6,7,8-tetrahydro-naphthalen-1-yloxy}-acetic acid;
{4-[4-Methyl-2-(4-trifluoromethyl-phenyl)-thiazol-5-ylmethylsulfanyl]-naphthalen-1-yloxy}-acetic acid;
2-[6-methyl-8-({4-methyl-2-[4-(trifluoromethyl)phenyl](1,3-thiazol-5-yl)}methylthio)chroman-5-yloxy]acetic acid;
2-[5-methyl-7-({4-methyl-2-[4-(trifluoromethyl)phenyl](1,3-thiazol-5-yl)}methylthio)-2,3-dihydrobenzo[b]furan-4-yloxy]acetic acid;
{5-Methyl-7-[4-methyl-2-(4-trifluoromethyl-phenyl)-thiazol-5-ylmethylsulfanyl]-indan-4-yloxy}-acetic acid;
{7-[4-Methyl-2-(4-trifluoromethyl-phenyl)-thiazol-5-ylmethylsulfanyl]-indan-4-yloxy}-acetic acid; and pharmaceutically acceptable salts thereof.

23. A pharmaceutical composition comprising a compound of claim 1 and one or more pharmaceutically acceptable carriers, diluents, or excipients.

24. A method of treating or controlling obesity in a mammal comprising administering to the mammal in need thereof a therapeutically effective amount of a compound of claim 1.

25. A method of treating or controlling hyperlipidemia in a mammal comprising administering to the mammal in need thereof a therapeutically effective amount of a compound of claim 1.

26. A method of treating or controlling hypercholesteremia in a mammal comprising administering to the mammal in need thereof a therapeutically effective amount of a compound of claim 1.

27. A method of treating or controlling atherosclerosis in a mammal comprising administering to the mammal in need thereof a therapeutically effective amount of a compound of claim 1.

28. A method of treating or controlling hypertriglyceridemia in a mammal comprising administering to the mammal in need thereof a therapeutically effective amount of a compound of claim 1.

29. A method of treating a patient exhibiting glucose disorders associated with circulating glucocorticoids, growth hormone, catecholamines, glucagon, or parathyroid hormone, comprising administering to the patient a therapeutically effective amount of a compound of claim 1.

30. A method of making the compound of claim 1, the method comprising, reacting:

wherein
X is a halogen;
$X^0$ and $X^1$ are independently O or S;
$Ar^1$ is substituted or unsubstituted aryl or heteroaryl;
T is a saturated or unsaturated, substituted or unsubstituted hydrocarbon chain or hydrocarbon-heteroatom chain having from 3 to 6 atoms wherein the carbon atom of position 2 is connected to the carbon atom of position 3 to form a five to eight member ring;

W is O, S, $CH_2$, $CR^4R^5$, $NR^3$, cycloalkylene, or heterocycloalkylene;

Y is absent, O, or $CR^4R^5$ wherein
Y is $CR^4R^5$ or absent when W is O, S, or $NR^3$; and
Y is O or absent when W is $CH_2$ or $CR^4R^5$;

$R^1$ and $R^2$ are independently hydrogen, lower alkyl, lower alkoxy, lower thioalkoxy, —$O(CH_2)_pCF_3$, halogen, nitro, cyano, —OH, —SH, —$CF_3$, —$OCF_3$, $S(O)_n$Alkyl, $S(O)_p$Aryl, —$(CH_2)_mOR^3$, —$(CH_2)_mNR^6R^7$, $COR^3$, —$CO_2H$, —$CO_2R^3$, or —$NR^6R^7$;

$R^3$ is hydrogen, alkyl, alkenyl, alkynyl, or aryl;

$R^4$ and $R^5$ are independently hydrogen, alkyl, alkenyl, alkynyl, or aryl, or joined together to form a 4 to 7 member ring having 0 to 3 heteroatoms;

$R^6$ and $R^7$ are independently hydrogen, alkyl, alkenyl, alkynyl, —COalkyl, —COaryl, cycloalkyl, —$CO_2$alkyl, —$CO_2$aryl, —$SO_2$alkyl, —$SO_2$aryl, or joined together to form a 4 to 7 member ring having 1 to 3 heteroatoms;

m is 0 to 5;

n is 0 to 5; and p is 0 to 2.

* * * * *